US012567499B2

(12) United States Patent
Son et al.

(10) Patent No.: US 12,567,499 B2
(45) Date of Patent: Mar. 3, 2026

(54) METHOD AND TERMINAL DEVICE FOR PROVIDING ORAL STATE INFORMATION INCLUDING PERIODONTITIS

(71) Applicant: SMARTOOTH KOREA CO., LTD., Seoul (KR)

(72) Inventors: Ho Jung Son, Seoul (KR); Myung Seon Ryou, Seoul (KR)

(73) Assignee: SMARTOOTH KOREA CO., LTD., Seoul (KR)

( * ) Notice: Subject to any disclaimer, the term of this patent is extended or adjusted under 35 U.S.C. 154(b) by 307 days.

(21) Appl. No.: 18/370,399

(22) Filed: Sep. 20, 2023

(65) Prior Publication Data

US 2024/0266030 A1 Aug. 8, 2024

(30) Foreign Application Priority Data

Feb. 3, 2023 (KR) ........................ 10-2023-0014718

(51) Int. Cl.
  *G16H 30/40*  (2018.01)
  *A61B 5/00*  (2006.01)
  *G06T 7/00*  (2017.01)

(52) U.S. Cl.
  CPC .......... *G16H 30/40* (2018.01); *A61B 5/4547* (2013.01); *G06T 7/0012* (2013.01); *G06T 2207/10116* (2013.01); *G06T 2207/30036* (2013.01)

(58) Field of Classification Search
None
See application file for complete search history.

(56) References Cited

U.S. PATENT DOCUMENTS

2002/0178032 A1* 11/2002 Benn ...................... G16H 10/60
                                                          705/2
2018/0206949 A1* 7/2018 Jordan ............... A61C 13/0004
                      (Continued)

FOREIGN PATENT DOCUMENTS

JP      2009-131313 A    6/2009
JP      2011-72573 A     4/2011
                      (Continued)

OTHER PUBLICATIONS

Tsuji Keien, JP-2020093061-A English Translation, Periodontal Disease Diagnosis Support Apparatus, and Method and Program for the Same (Year: 2020).*
                      (Continued)

*Primary Examiner* — Miya J Cato
(74) *Attorney, Agent, or Firm* — United One Law Group LLC; Kongsik Kim; Jhongwoo Peck

(57) ABSTRACT

Provided are method of providing oral state information including periodontitis and a terminal device for executing the method. The method is executed in a processor based device and comprises: extracting a first gum bone line from user's first oral image captured in a first period; extracting a second gum bone line from user's second oral image captured in a second period after the first period; calculating a height difference in gum bones for each of the user's teeth based on the second gum bone line and the first gum bone line; selecting a first tooth having a height difference in gum bones that is more than a predetermined threshold value from among user's teeth; generating information on periodontitis deterioration numeric values of the first tooth based on the height difference of the gum bones in the first tooth; generating a result oral image by representing information on periodontitis deterioration numeric values of the first tooth in a first information representation region which is adjacent to a first tooth region that corresponds to the first
                      (Continued)

tooth in the second oral image; and displaying the result oral image.

13 Claims, 23 Drawing Sheets

(56) References Cited

U.S. PATENT DOCUMENTS

| | | | | |
|---|---|---|---|---|
| 2022/0180447 A1* | 6/2022 | Kearney | ................. | G06N 3/047 |
| 2023/0368907 A1* | 11/2023 | Son | ...................... | A61B 5/0534 |
| 2024/0083985 A1* | 3/2024 | Han | ................... | C07K 16/1203 |

FOREIGN PATENT DOCUMENTS

| | | | |
|---|---|---|---|
| JP | 2011072573 A | * | 4/2011 |
| JP | 2017-525408 A | | 9/2017 |
| JP | 2020-93061 A | | 6/2020 |
| JP | 2020093061 A | * | 6/2020 |
| KR | 10-2288592 B1 | | 8/2021 |
| KR | 10-2311395 B1 | | 10/2021 |
| KR | 10-2368681 B1 | | 2/2022 |
| KR | 10-2022-0040023 A | | 3/2022 |
| KR | 10-2421739 B1 | | 7/2022 |
| WO | 2015/008491 A1 | | 3/2017 |

OTHER PUBLICATIONS

Tsuji Keien, JP-2011072573-A English Translation, Management Support System for Periodontal Disease Using Dental X-Rays (Year: 2011).*

* cited by examiner

FIG. 2

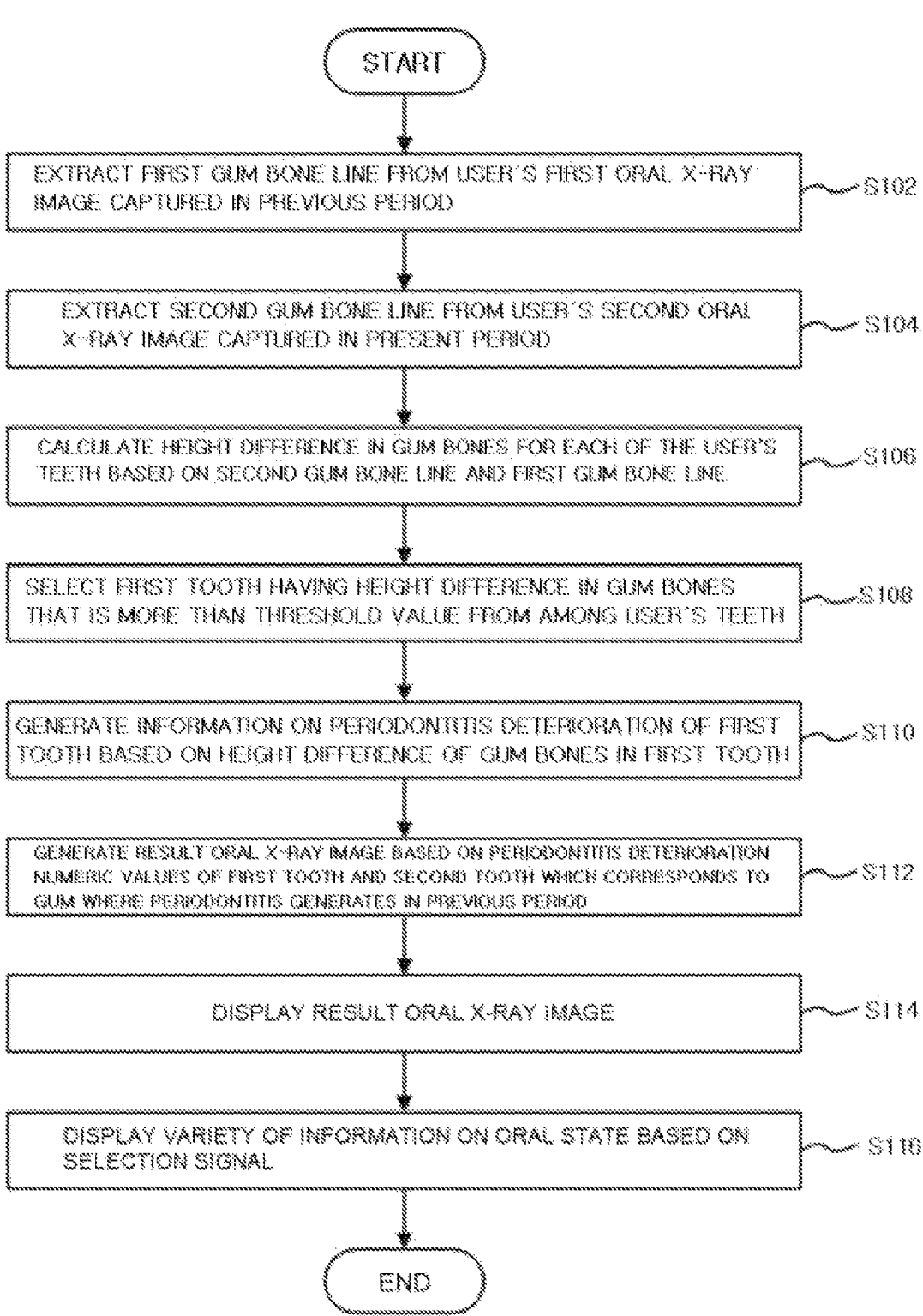

START

EXTRACT FIRST GUM BONE LINE FROM USER'S FIRST ORAL X-RAY IMAGE CAPTURED IN PREVIOUS PERIOD —— S102

EXTRACT SECOND GUM BONE LINE FROM USER'S SECOND ORAL X-RAY IMAGE CAPTURED IN PRESENT PERIOD —— S104

CALCULATE HEIGHT DIFFERENCE IN GUM BONES FOR EACH OF THE USER'S TEETH BASED ON SECOND GUM BONE LINE AND FIRST GUM BONE LINE —— S106

SELECT FIRST TOOTH HAVING HEIGHT DIFFERENCE IN GUM BONES THAT IS MORE THAN THRESHOLD VALUE FROM AMONG USER'S TEETH —— S108

GENERATE INFORMATION ON PERIODONTITIS DETERIORATION OF FIRST TOOTH BASED ON HEIGHT DIFFERENCE OF GUM BONES IN FIRST TOOTH —— S110

GENERATE RESULT ORAL X-RAY IMAGE BASED ON PERIODONTITIS DETERIORATION NUMERIC VALUES OF FIRST TOOTH AND SECOND TOOTH WHICH CORRESPONDS TO GUM WHERE PERIODONTITIS GENERATES IN PREVIOUS PERIOD —— S112

DISPLAY RESULT ORAL X-RAY IMAGE —— S114

DISPLAY VARIETY OF INFORMATION ON ORAL STATE BASED ON SELECTION SIGNAL —— S116

END

310

320

FIG. 4
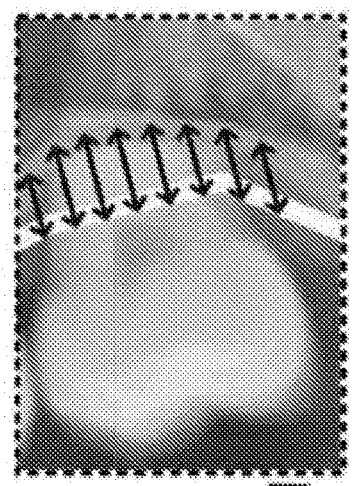
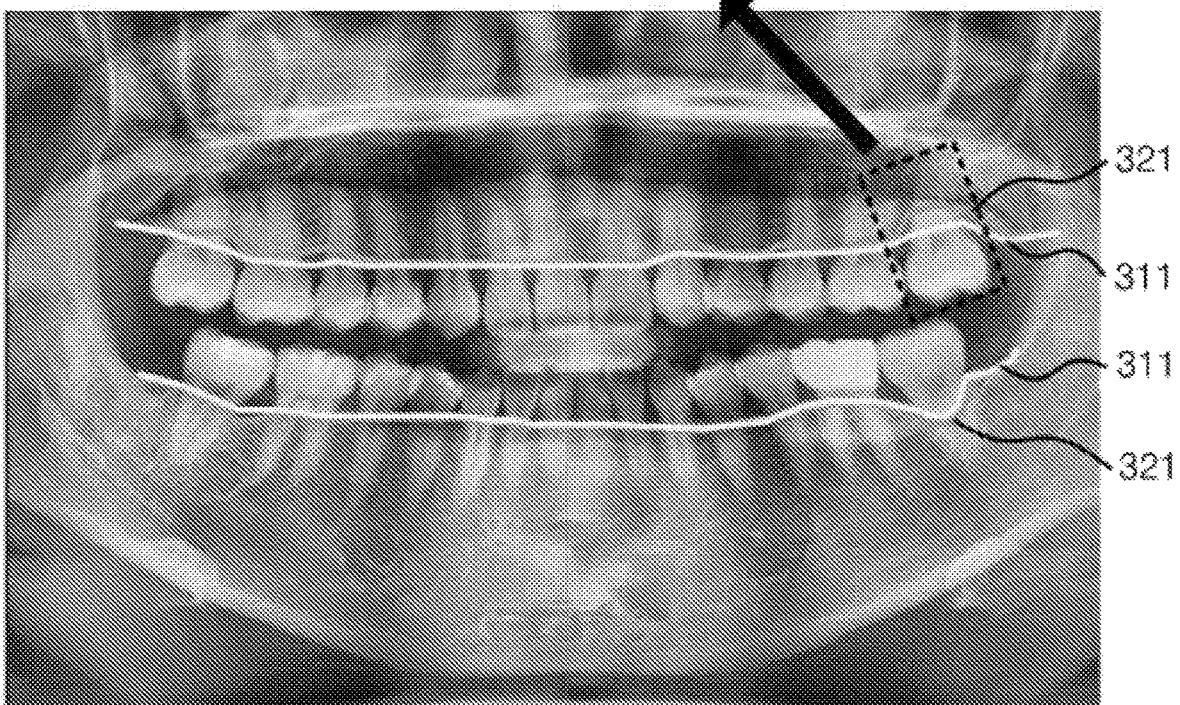
321
311
311
321

FIG. 13

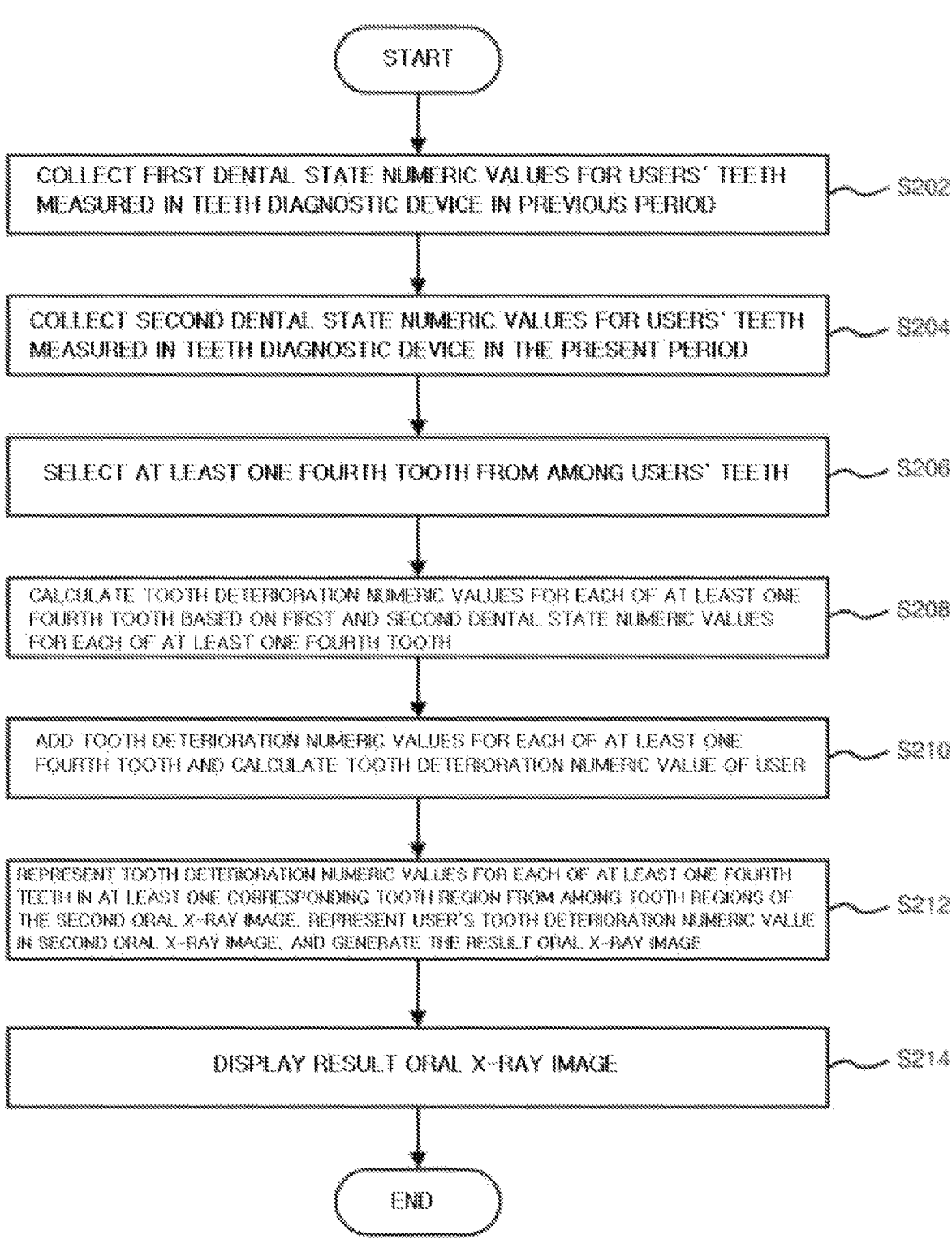

START

COLLECT FIRST DENTAL STATE NUMERIC VALUES FOR USERS' TEETH MEASURED IN TEETH DIAGNOSTIC DEVICE IN PREVIOUS PERIOD —— S202

COLLECT SECOND DENTAL STATE NUMERIC VALUES FOR USERS' TEETH MEASURED IN TEETH DIAGNOSTIC DEVICE IN THE PRESENT PERIOD —— S204

SELECT AT LEAST ONE FOURTH TOOTH FROM AMONG USERS' TEETH —— S206

CALCULATE TOOTH DETERIORATION NUMERIC VALUES FOR EACH OF AT LEAST ONE FOURTH TOOTH BASED ON FIRST AND SECOND DENTAL STATE NUMERIC VALUES FOR EACH OF AT LEAST ONE FOURTH TOOTH —— S208

ADD TOOTH DETERIORATION NUMERIC VALUES FOR EACH OF AT LEAST ONE FOURTH TOOTH AND CALCULATE TOOTH DETERIORATION NUMERIC VALUE OF USER —— S210

REPRESENT TOOTH DETERIORATION NUMERIC VALUES FOR EACH OF AT LEAST ONE FOURTH TEETH IN AT LEAST ONE CORRESPONDING TOOTH REGION FROM AMONG TOOTH REGIONS OF THE SECOND ORAL X-RAY IMAGE, REPRESENT USER'S TOOTH DETERIORATION NUMERIC VALUE IN SECOND ORAL X-RAY IMAGE, AND GENERATE THE RESULT ORAL X-RAY IMAGE —— S212

DISPLAY RESULT ORAL X-RAY IMAGE —— S214

END

| | TOOTH A | TOOTH B | TOOTH C | TOOTH D | TOOTH E | TOOTH F | TOOTH G |
|---|---|---|---|---|---|---|---|
| FIRST MEASUREMENT PERIOD | 29 | 20 | 12 | 58 | 15 | 0 | 72 |
| SECOND MEASUREMENT PERIOD | 31 | 25 | 13 | 65 | 26 | 7 | 4 |

METHOD AND TERMINAL DEVICE FOR PROVIDING ORAL STATE INFORMATION INCLUDING PERIODONTITIS

CROSS-REFERENCE TO RELATED PATENT APPLICATION

This application claims the benefit of Korean Patent Application No. 10-2023-0014718, filed on Feb. 3, 2023, in the Korean Intellectual Property Office, the disclosure of which is incorporated herein in its entirety by reference.

BACKGROUND OF THE INVENTION

1. Field of the Invention

One or more embodiments of the present invention relate to a method of providing oral state information including periodontitis and a terminal device for performing the same.

2. Description of the Related Art

Eating is one of the most important factors for people and in order to efficiently eat, teeth and gums need to be kept healthy. In order to manage the oral cavity in a health way, proper teeth brushing and use of dental floss are needed.

That is, if users do not properly brush their teeth or use dental floss after they eat, food particles are left in their mouth and the bacteria may increase in the mouth. Accordingly, infectious diseases such as decayed tooth may be generated. In addition, various minerals are deposited and tartar, dental plaque, and gum diseases may be generated.

In particular, periodontal diseases appear in periodontal tissues such as the gum that surrounds teeth, periodontal ligament, and gum bone (alveolar bone) and are classified into gingivitis and periodontitis according to progression of disease. An inflammation which is limited to the gum, that is, soft tissue, and relatively mild with quick recovery is referred to as gingivitis and an inflammation which progresses to the gum and surroundings of alveolar bone is referred to as periodontitis.

Generally, a hand tool such as a periodontal probe is used to diagnose periodontitis in such a way that a length of the periodontal probe that is inserted into the gum of a user (patient) and bleeding are identified. Also, a dental radiographic image of the gum is directly read by medical staff to diagnose periodontitis.

However, if the periodontal probe is used, bleeding is easily generated due to periodontitis so that a periodontal pocket depth may be measured deeper than it is, a considerable amount of time may be required for diagnosing, and users may feel inconvenient. In addition, if a dental radiographic image is used, inaccurate diagnosis may be made due to subjective valuation from medical staffs who read the radiographic image.

Moreover, it is necessary to regularly check oral state so that accurate oral diagnosis may be available. In particular, medical staffs need to compare previous oral state to current oral state and to perform oral diagnosis. However, a technique which compares the previous oral state to the current oral state and automatically provides meaningful notification information does not exist.

SUMMARY OF THE INVENTION

The present invention provides a method of providing oral state information to users and medical staffs by simply and easily producing comparison information on previous and current oral states based on a dental image of a user taken regularly, and a terminal device for performing the same.

The present invention also provides a method of providing oral state information through which meaningful information relating to the gum, in particular, numeric information on deterioration of periodontitis may be provided to users and medical staffs based on measured gum state, and a terminal device for performing the same.

According to an aspect of the present invention, there is provided a method of providing periodontitis information executed in a processor based device including: extracting a first gum bone line from user's first oral image captured in a first period; extracting a second gum bone line from user's second oral image captured in a second period after the first period; calculating a height difference in gum bones for each of the user's teeth based on the second gum bone line and the first gum bone line; selecting a first tooth having a height difference in gum bones that more than a predetermined threshold value from among user's teeth; generating information on periodontitis deterioration numeric values of the first tooth based on the height difference of the gum bones in the first tooth; generating a result oral image by representing information on periodontitis deterioration numeric values of the first tooth in a first information representation region which is adjacent to a first tooth region that corresponds to the first tooth in the second oral image; and displaying the result oral image.

According to another aspect of the present invention, there is provided a terminal device including: a memory for storing computer readable commands; a processor embodied to execute the commands; and a display unit for displaying execution results of the commands. Here, the processor extracts a first gum bone line from user's first oral image captured in a first period, extracts a second gum bone line from user's second oral image captured in a second period after the first period, calculates a height difference in gum bones for each of the user's teeth based on the second gum bone line and the first gum bone line, selects a first tooth having a height difference in gum bones that is more than a predetermined threshold value from among user's teeth, generates information on periodontitis deterioration numeric values of the first tooth based on the height difference of the gum bones in the first tooth, generates a result oral image by representing information on periodontitis deterioration numeric values of the first tooth in a first information representation region which is adjacent to a first tooth region that corresponds to the first tooth in the second oral image, and displays the result oral image.

According to another aspect of the present invention, there is provided a method of providing oral state information executed in a processor based device including: generating a first result image that represents periodontitis deterioration numeric values of user's gums; generating a second result image that represents tooth deterioration numeric values of user's teeth'; and displaying at least one of the first result image and the second result image. Here, generating the first result image includes: extracting a first gum bone line from user's first oral image captured in a first period; extracting a second gum bone line from user's second oral image captured in a second period after the first period; calculating a height difference in gum bones for each of the user's teeth based on the second gum bone line and the first gum bone line; selecting a first tooth having a height difference in gum bones that is more than a predetermined threshold value from among user's teeth; generating information on periodontitis deterioration numeric values of the first tooth based on the height difference of the gum bones in the first tooth; and generating the first result image by representing information on periodontitis deterioration numeric values of the first tooth in a first information representation region which is adjacent to a first tooth region that corresponds to the first tooth in the second oral image. Also, generating the second result image includes: calculating a tooth deterioration numeric value for each of the at least one tooth in the second period based on first dental state numeric values for each of the at least one user's tooth in the first period and second dental state numeric values for each of the at least one tooth in the second period, calculating user's tooth deterioration numeric value by adding the tooth deterioration numeric value for each of the at least one fourth tooth, representing the tooth deterioration numeric value for each of the at least one tooth in at least one corresponding tooth region from among tooth regions in the second oral image, representing user's tooth deterioration numeric values in the second oral image, and generating the second result image.

BRIEF DESCRIPTION OF THE DRAWINGS

FIG. 2 is a flowchart generally illustrating a method of operating a periodontitis mode, that is, a method of providing periodontitis information according to an embodiment of the present invention;

FIG. 4 illustrates an example where first and second gum bone lines are indicated on a second oral x-ray image according to an embodiment of the present invention;

FIG. 13 is a flowchart generally illustrating a method of operating a dental state mode, that is, a method of providing dental state information according to an embodiment of the present invention;

DETAILED DESCRIPTION OF THE INVENTION

Figure 1:
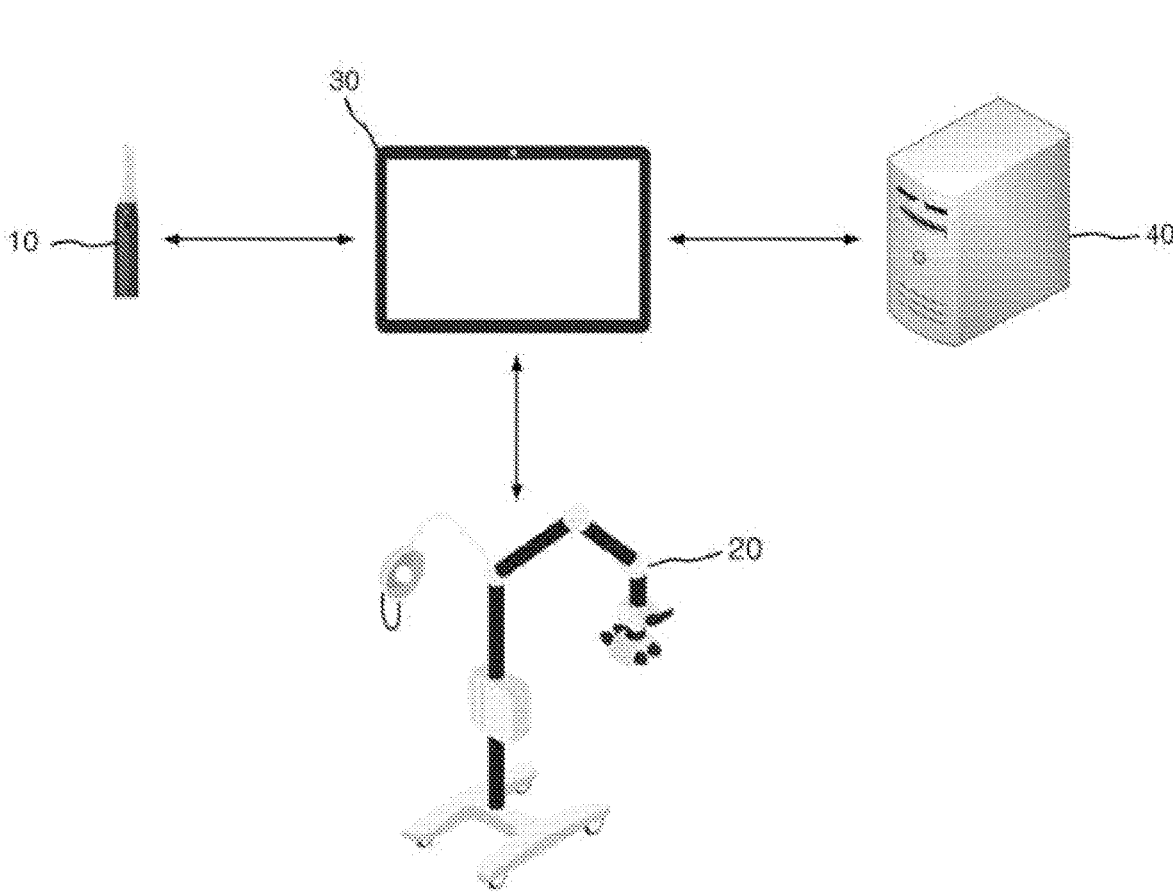
FIG. 1 schematically illustrates an oral management system according to an embodiment of the present invention.

Hereinafter, the present invention may be embodied in many different forms and may have various embodiments and thereby, particular embodiments are illustrated in the drawings for fully describing the invention. It should be understood, however, that there is no intent to limit exemplary embodiments to the particular forms disclosed, but on the contrary, exemplary embodiments are to cover all modifications, equivalents, and alternatives falling within the scope of the invention. In the drawings, like reference numerals denote like elements.

It will be understood that, although the terms "first", "second", etc. may be used herein to describe various elements, these elements should not be limited by these terms. These terms are only used to distinguish one element from another. As used herein, the term "and/or," includes any and all combinations of one or more of the associated listed items.

The terminology used herein is for the purpose of describing particular embodiments only and is not intended to be limiting of exemplary embodiments. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, components, and/or groups thereof, but do not preclude the presence or addition of one or more other features, integers, steps, operations, elements, components, and/or groups thereof.

Unless defined differently, all terms used in the description including technical and scientific terms have the same meaning as generally understood by those skilled in the art. Terms as defined in a commonly used dictionary should be construed as having the same meaning as in an associated technical context, and unless defined apparently in the description, the terms are not ideally or excessively construed as having formal meaning.

Hereinafter, the present invention will be described in more detail with reference to the accompanying drawings.

FIG. 1 schematically illustrates an oral management system 1 according to an embodiment of the present invention.

Referring to FIG. 1, the oral management system 1 according to an embodiment of the present invention may include a teeth diagnostic device 10, an x-ray device 20, a terminal device 30, and a management server 40.

Hereinafter, functions of each element will be described in more detail.

The teeth diagnostic device 10 may measure dental states of user, for example, decayed teeth. For example, the teeth diagnostic device 10 may be a mobile device that measures dental states of users by using an optical sensor. However, the present invention is not limited thereto and all type of teeth diagnostic devices may be applied to the present invention. For example, the teeth diagnostic device 10 may include a teeth diagnostic device having a PH measurement method, a camera-based teeth diagnostic device, or a teeth diagnostic device linked with x-ray.

The teeth diagnostic device 10 may include a communication unit, a state measurement unit, and a processor, wherein the communication unit communicates with external devices by using a wired and wireless method, the state measurement unit measures dental state information in a probe form, and a processor controls the communication unit and the state measurement unit.

Here, the dental state information may correspond to dental state numeric values, for example, decayed tooth numeric values. The dental state numeric values may have any one value from 0 through 99 points. The higher the dental state numeric values, the further decayed tooth progress. The lower the dental state numeric values, the healthier the dental state.

The x-ray device 20 may capture an oral x-ray image of a user (patient). The x-ray device 20 may communicate with the terminal device 30 and/or the management server 40 by using a wired and wireless method and may transmit the captured oral x-ray image to the terminal device 30 and/or the management server 40.

The terminal device 30 may be owned by medical staffs. For example, as illustrated in FIG. 1, the terminal device 30 may be a smart device such as a smart phone or a smart pad. However, the present invention is not limited thereto and the terminal device 30 may be a personal computer (PC) including a display unit. Also, the terminal device 30 may owned by a user.

The terminal device 30 may receive the dental state information of a user measured from the teeth diagnostic device 10 and may generate a user's dental result image that represents tooth deterioration numeric values, which will be described later, based on the received dental state information. Also, the terminal device 30 may receive the oral x-ray image transmitted from the x-ray device 20 and may generate a periodontitis result image that represents periodontitis deterioration numeric values, which will be described later, based on the received oral x-ray image. In addition, as will be described later, the management server 40 may generate a periodontitis result image based on the oral x-ray image transmitted from the x-ray device 20 and the terminal device 30 may receive the periodontitis result image from the management server 40. An oral result image including the dental result image and the periodontitis result image may be output visually to users.

The terminal device 30 may include a communication unit, a display unit, a memory, and a processor. The communication unit communicates with external devices by using a wired and wireless method and may include a telecommunication module and a near field communication module (for example, a Bluetooth module and a WiFi module). The display unit may display an oral result image and may also receive a touch signal from a user. The memory may store application (computer program or recording medium) related command or data. The processor may include at least one of a central processing unit, an application processor, and a communication processor and may control other components of the terminal device 30 and/or perform a communication related arithmetic operation or data processing.

The management server 40 may receive and store various information stored in the terminal device 30 and process various information relating to oral state. As described above, the management server 40 may generate the periodontitis result image based on the oral x-ray image transmitted from the x-ray device 20. The management server 40 may include a communication unit and a processor.

Meanwhile, the terminal device 30 may be operated in a periodontitis mode which provides the periodontitis result image (a first result image) including the periodontitis information to a user and a medical staff and may also be operated in a dental state mode which provides a dental result image (a second result image) including the dental state information to a user and a medical staff. That is, a method of providing oral state information executed in the terminal device 30 or the terminal device 30 linked with the management server 40 may include generating the first result image which represents periodontitis deterioration numeric values of users' gums, generating the second result image which represents tooth deterioration numeric values of users' tooth, and displaying at least one of the first result image and the second result image. Here, in displaying at least one of the first result image and the second result image, the first result image or the second result image may be displayed by selection made from medical staffs.

Hereinafter, the method of providing oral state information including the periodontitis information and the dental state information will be described in more detail with reference to FIGS. 2 through 15.

FIG. 2 is a flowchart generally illustrating a method of operating the periodontitis mode, that is, a method of providing periodontitis information according to an embodiment of the present invention.

Here, all steps in the method of FIG. 2 may be executed in the terminal device 30 or a part of the steps of FIG. 2 may be executed in the management server 40. The part of the steps may be step S102 through step S112. Hereinafter, for convenience of description, it is assumed that steps in FIG. 2 are all executed in the terminal device 30.

As described above, the periodontitis is a disease where an inflammation progresses to gums and gum bones and a degree of the periodontitis is proportional to a degree of submersion of gums or gum bones. That is, as the periodontitis get worse, a degree of submersion of gum bones increases. In this regard, according to the present invention, a degree of the periodontitis may be determined based on a degree of submersion of gum bones. Hereinafter, processes performed in each step will be described in more detail.

In step S102, the terminal device 30 may extract a first gum bone line from a user's first oral x-ray image captured in a previous period.

In step S104, the terminal device 30 may extract a second gum bone line from a user's second oral x-ray image captured in a present period.

Here, the previous period (that is, a first period) and the present period (that is, a second period) correspond to a particular day and the term between the previous period and the present period may be approximately 4 weeks. However, the present invention is not limited thereto.

Also, the gum bone line may denote a line connecting user's gum bones in one line. For example, the gum bone line may be extracted based on each pixel value of the oral x-ray images. However, the present invention is not limited thereto and various methods of extracting gum bone lines may be applied to the present invention.

Figure 3A:
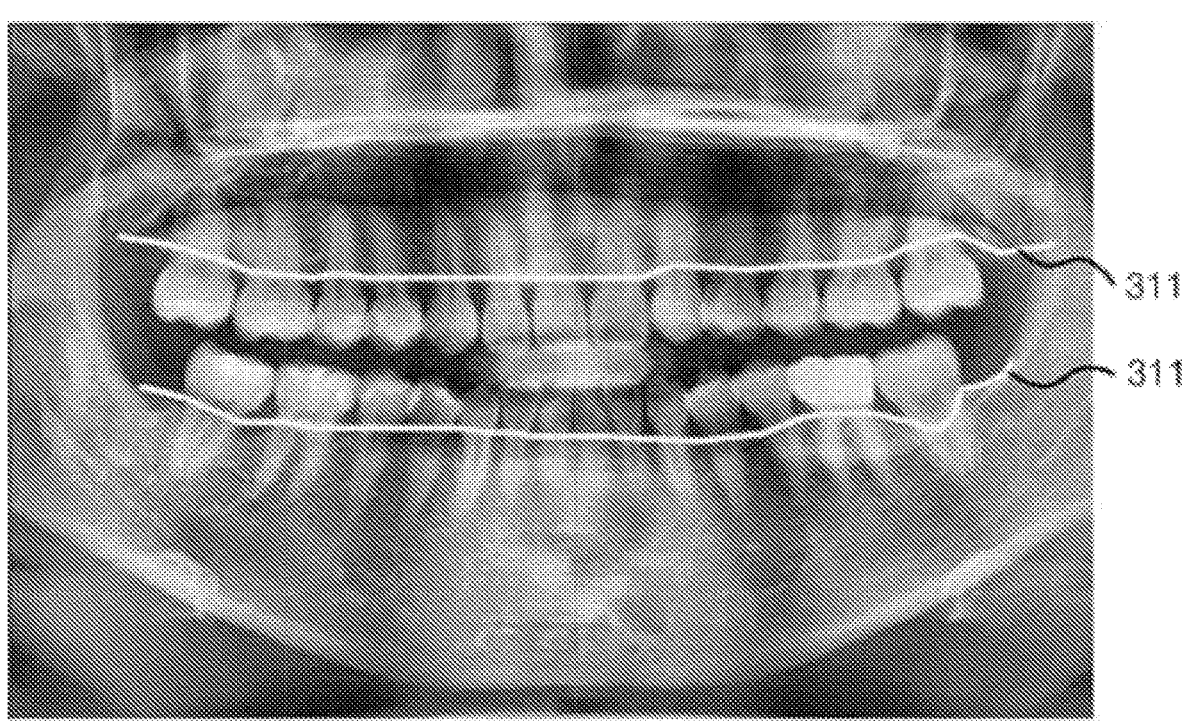
FIGS. 3A and 3B illustrate examples of gum bone lines extracted from oral x-ray images according to an embodiment of the present invention.
Figure 3B:
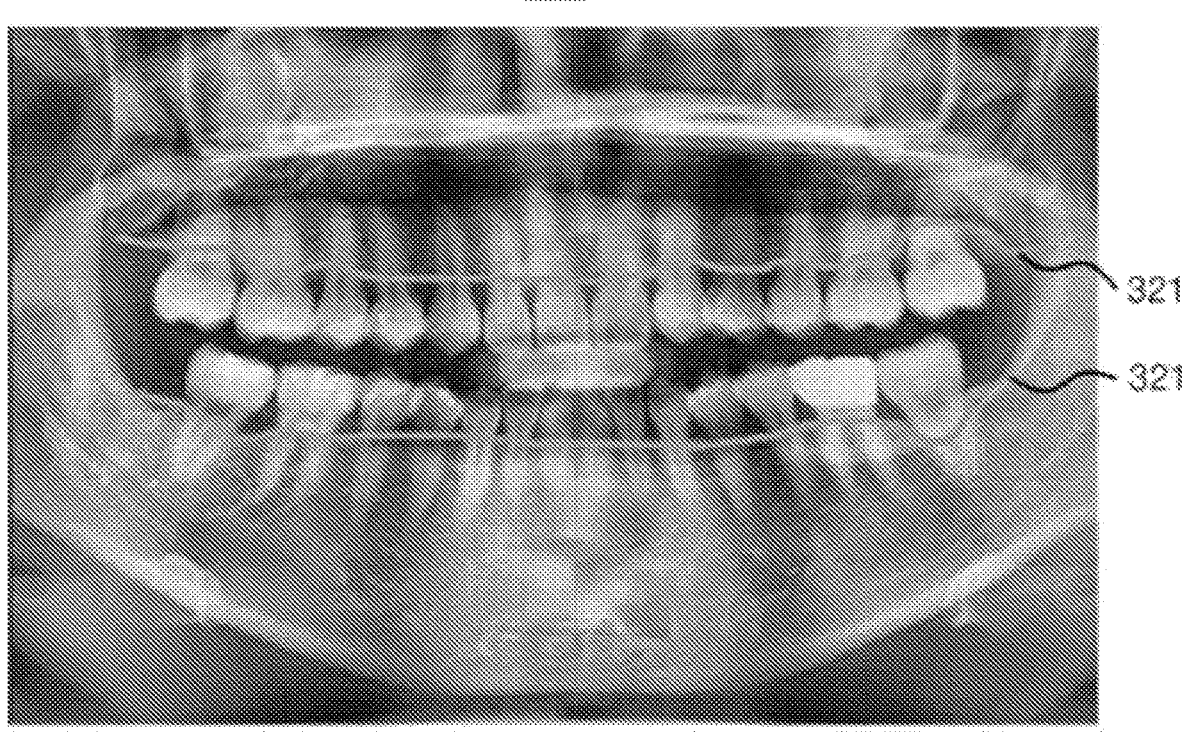

FIGS. 3A and 3B illustrate examples of gum bone lines extracted from oral x-ray images according to an embodiment of the present invention.

FIG. 3A illustrates a first gum bone line 311 extracted from a first oral x-ray image 310 captured in a previous period and FIG. 3B illustrates a second gum bone line 321 extracted from a second oral x-ray image 320 captured in a present period.

The oral x-ray images illustrated in FIGS. 3A and 3B are not displayed to users or medical staffs and are used only for simply describing an extraction concept of the gum bone lines 311 and 321.

Referring back to FIG. 2, the terminal device 30 may calculate a height difference in gum bones by each of users' teeth based on the second gum bone line 321 and the first gum bone line 311 in step S106.

FIG. 4 illustrates an example where the first and second gum bone lines 311 and 321 are indicated on the second oral x-ray image 320 according to an embodiment of the present invention.

Referring to FIG. 4, the terminal device 30 may calculates a height difference in gum bones of tooth A in such a way that a plurality of sample points is selected with respect to tooth A from among teeth illustrated in the second oral x-ray image 320, lengths (that is, a vertical length) of the second gum bone line 321 and the first gum bone line 311 are calculated with respect to the plurality of sample points, and lengths of top N (N is an integer above 1) from among lengths of the plurality of sample points are averaged.

The oral x-ray image illustrated in FIG. 4 is not displayed to users or medical staffs and are used only for simply describing an extraction concept of the gum bone lines 311 and 321.

Referring back to FIG. 2, the terminal device 30 may select a first tooth having a height difference in gum bones that is more than a predetermined threshold value from among user's teeth in step S108.

Here, the first tooth may be at least one. Also, the threshold value may be a reference value for determining whether the second gum bone line 321 in the present period is significantly distinguished from the first gum bone line 311 in the previous period. For example, the threshold value may be 0.4.

In step S110, the terminal device 30 may generate information on periodontitis deterioration of the first tooth based on the height difference of the gum bones in the first tooth.

That is, as described above, and a degree of the periodontitis is proportional to a degree of submersion of gum bones. Accordingly, the terminal device 30 may determine whether periodontitis, which is generated or may be generated in the gum of the first tooth, is deteriorated based on a difference between the height of the gum bones in the first tooth in the present period and the height of the gum bones in the first tooth in the previous period.

According to an embodiment of the present invention, the periodontitis deterioration numeric values may be a height difference of gum bones in the first tooth. According to another embodiment of the present invention, the periodontitis deterioration numeric values may be a height difference level that corresponds to the height difference of gum bones in the first tooth. For example, the height difference level may include first through third levels, wherein the section of the height difference of gum bones in the first level may be 0.5 mm through 0.8 mm, the section of the height difference of gum bones in the second level may be 0.8 mm through 1.1 mm, and the section of the height difference of gum bones in the third level may be above 1.1 mm.

In step S112, the terminal device 30 may generate a result oral x-ray image (the first result image) based on the periodontitis deterioration numeric values of the first tooth and a second tooth which corresponds to the gum where periodontitis generates in the previous period. Then, the terminal device 30 may display the result oral x-ray image in step S114.

Figure 5A:
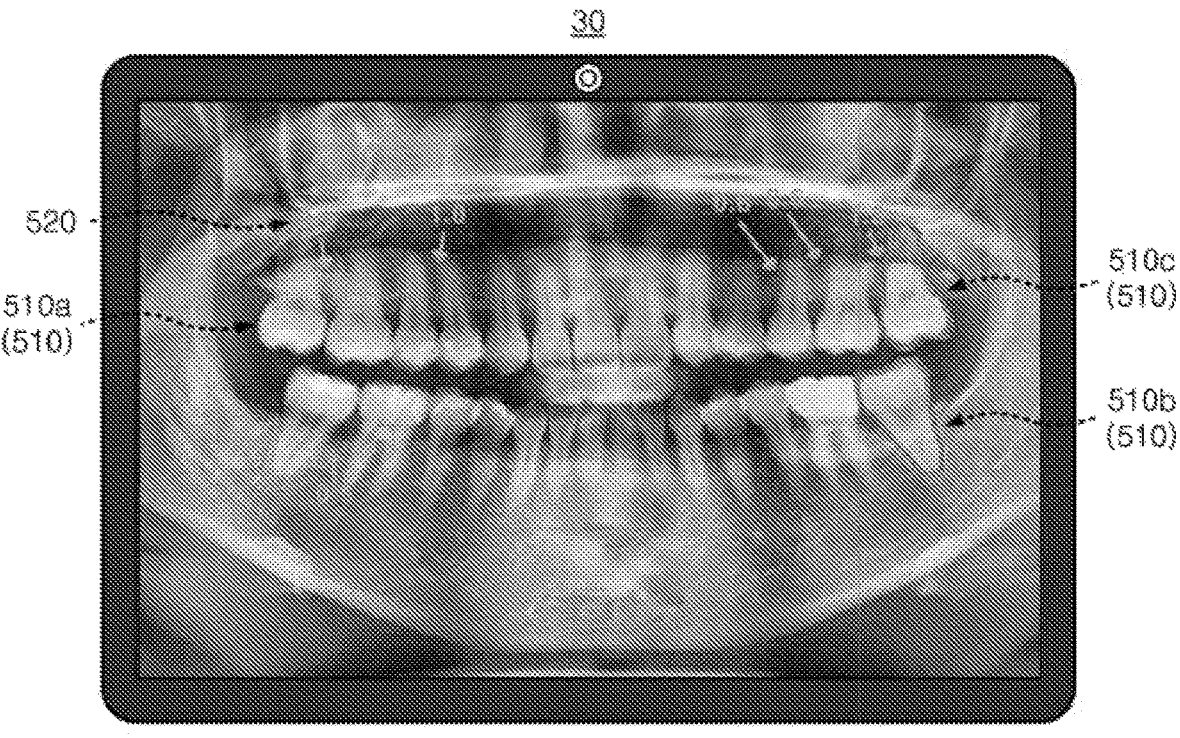
FIGS. 5A and 5B illustrate examples of result oral x-ray images displayed on a terminal device according to an embodiment of the present invention.
Figure 5B:
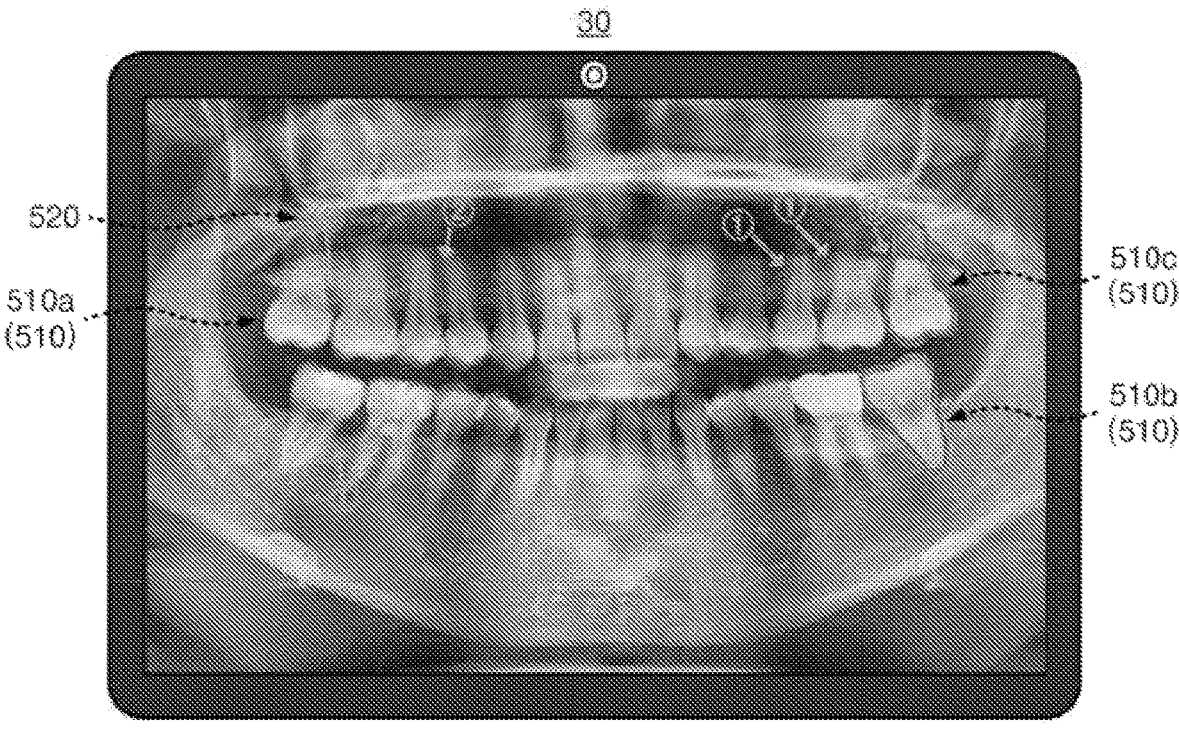

FIGS. 5A and 5B illustrate examples of the result oral x-ray images displayed on the terminal device 30 according to an embodiment of the present invention.

More specifically, FIG. 5A illustrates the result oral x-ray image where the periodontitis deterioration numeric values are the height difference in gum bones of teeth and FIG. 5B illustrates the result oral x-ray image where the periodontitis deterioration numeric values are the height difference level of teeth. Hereinafter, for convenience of description, it is assumed that the periodontitis deterioration numeric values are represented as in FIG. 5A.

Referring to FIGS. 5A and 5B, the second oral x-ray image may include a tooth region 510 that respectively corresponds to users' teeth. The tooth region 510 include a first tooth region 510A and a second tooth region 510B.

The first tooth region 510A may be the tooth region 510 that corresponds to the first tooth having the height difference in gum bones that is more than a threshold value. Here, in order to represent the periodontitis deterioration numeric values that corresponds to the height difference in gum bones, a first information representation region 520 may be represented to be adjacent to the first tooth region 510A.

The terminal device 30 may generate a result oral x-ray image in such a way that the periodontitis deterioration numeric values of the first tooth are represented in the first information representation region 520 of the second oral x-ray image, wherein the first information representation region 520 is adjacent to the first tooth region 510A that corresponds to the first tooth. Here, the terminal device 30 may represent the first information representation region 520 with a predetermined first color, for example, blue.

The second tooth region 510B may be the tooth region 510 for the second tooth that corresponds to the gum where periodontitis is diagnosed in the previous period. Here, periodontitis may be diagnosed by medical staffs or the method of providing periodontitis information executed in the previous period.

The terminal device 30 may represent the second tooth region 510B that corresponds to the second tooth to be distinguished from other tooth region and may generate the result oral x-ray image. Here, the terminal device 30 may represent a boundary line of the second tooth region 510B with a predetermined third color, for example, red.

The height difference in gum bones of the second tooth may be more than a threshold value or may not be more than a threshold value. Hereinafter, for convenience of description, the second tooth having the height difference in gum bones that is more than a threshold value is referred to a "third tooth." That is, the third tooth may be the first tooth and the second tooth.

Accordingly, a boundary line of a third tooth region 510C that corresponds to the third tooth may be represented with the third color (red) and the first information representation region 520 may be represented to be adjacent to the third tooth region 510C.

For example, in the method of providing periodontitis information according to an embodiment of the present invention, the periodontitis deterioration numeric values of all users' teeth are not represented in the result oral x-ray image and instead, the periodontitis deterioration numeric values of the first tooth having the height difference in gum bones that is more than a threshold value, that is, the first tooth that corresponds to the gum where periodontitis may be further progressed, may be represented in the result oral x-ray image. As only limited information is represented in the result oral x-ray image, medical staffs and users may easily identify the periodontitis deterioration numeric values of the first tooth.

Referring back to FIG. 2, the terminal device 30 may display a variety of information on oral state based on a selection signal input from medical staffs (or users) in step S116.

Here, when the terminal device 30 is a smart device, the selection signal may correspond to a touch signal and when the terminal device 30 is a personal computer (PC), the selection signal may correspond to a mouse click signal.

Hereinafter, examples in step S116 will be described in more detail. Here, it is assumed that the terminal device 30 is a smart device.

FIGS. 6A through 9B illustrate examples of displaying information relating to the third tooth region 510C according to an embodiment of the present invention.

Figure 6A:
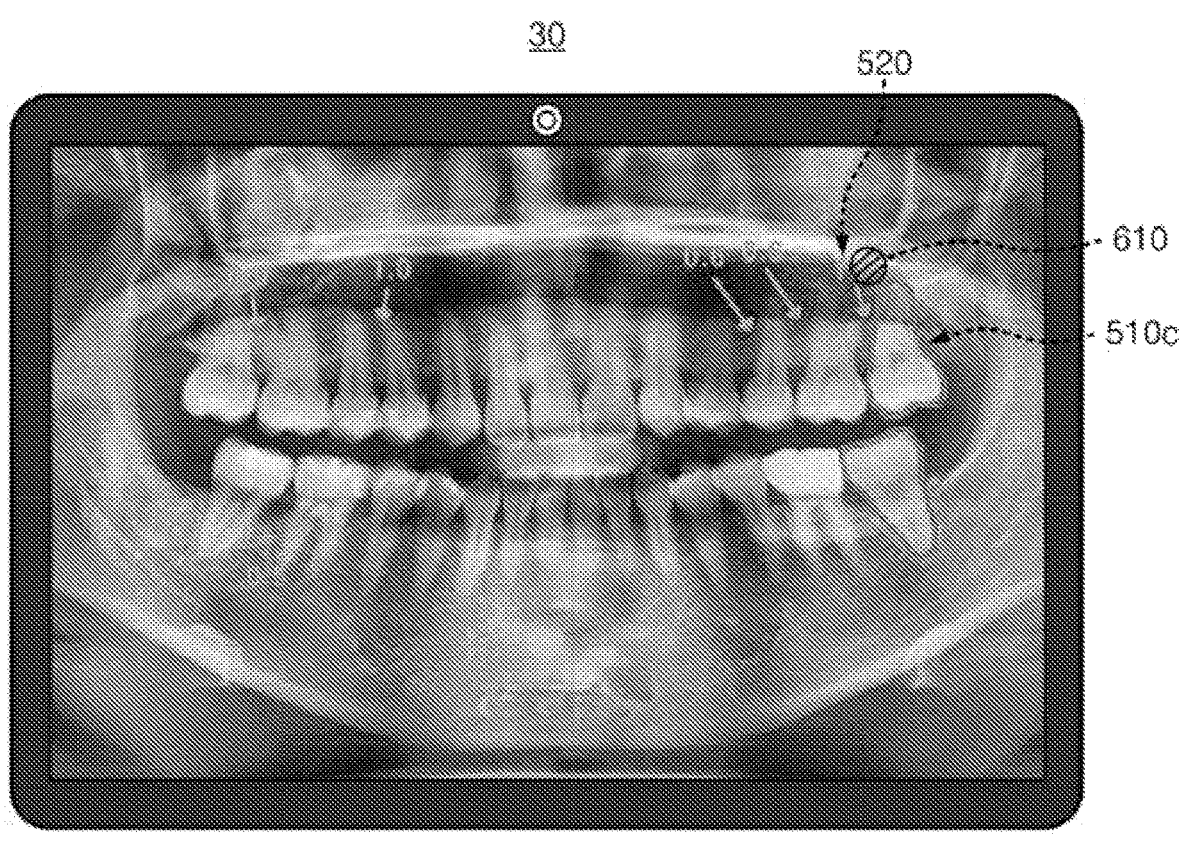
FIGS. 6A through 12B illustrate examples of displaying information relating to a tooth region according to an embodiment of the present invention.
Figure 6B:
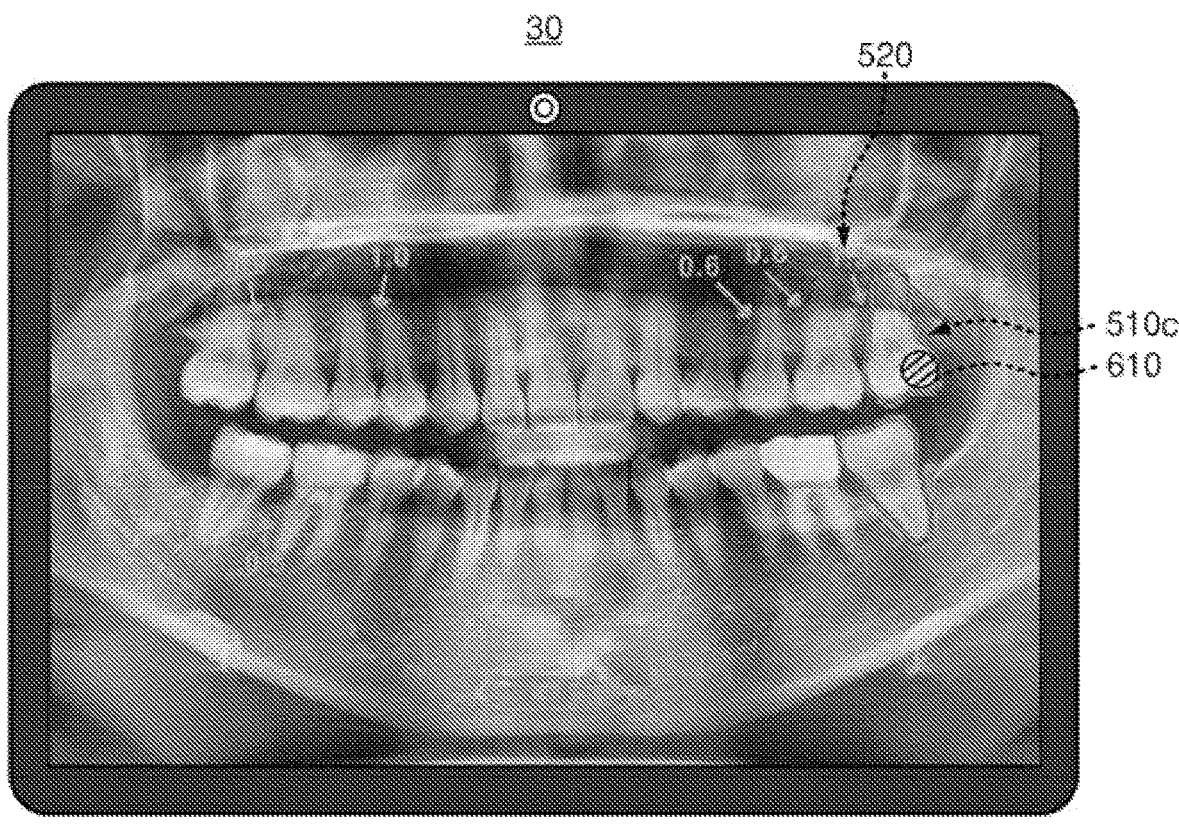

Referring to FIGS. 6A and 6B, a selection signal 610 from a medical staff may be input to the display unit of the terminal device 30.

More specifically, referring to FIG. 6A, the selection signal 610 may be input to the first information representation region 520 which is adjacent to the third tooth region 510C. Also, referring to FIG. 6B, the selection signal 610 may be directly input to the third tooth region 510C.

Figure 7A:
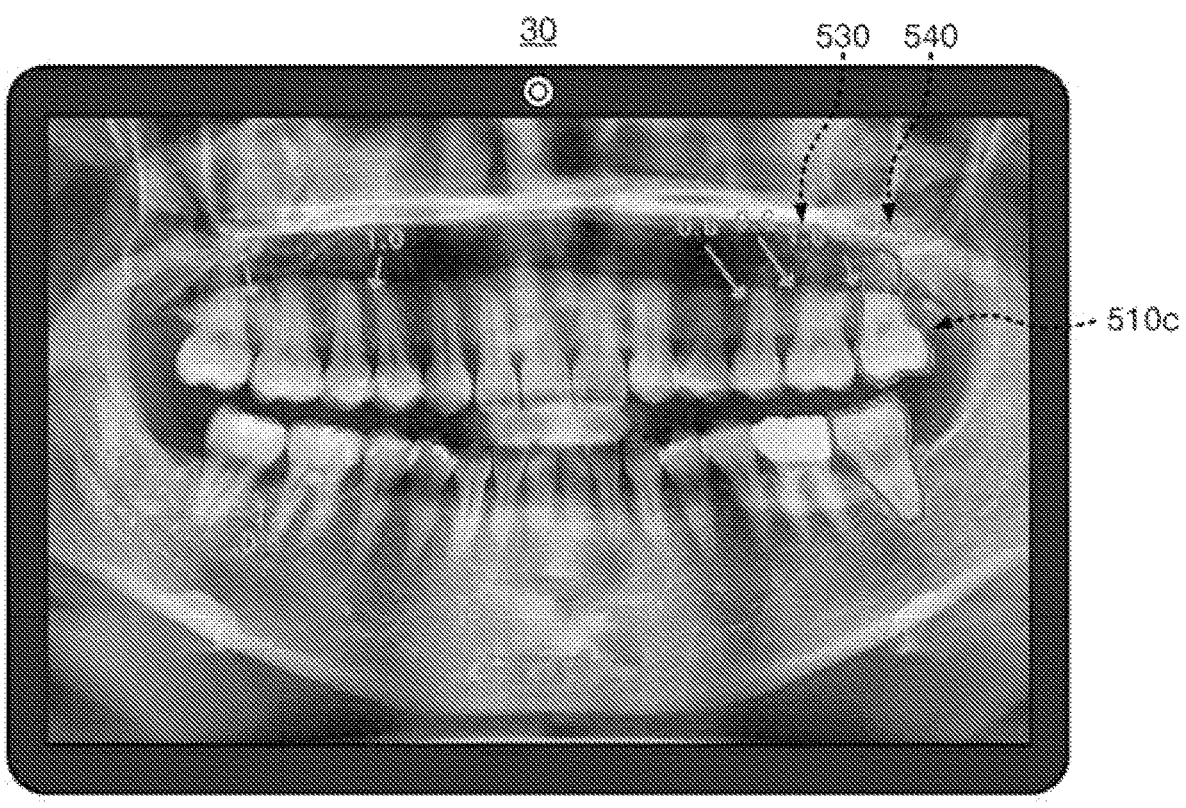
Figure 7B:
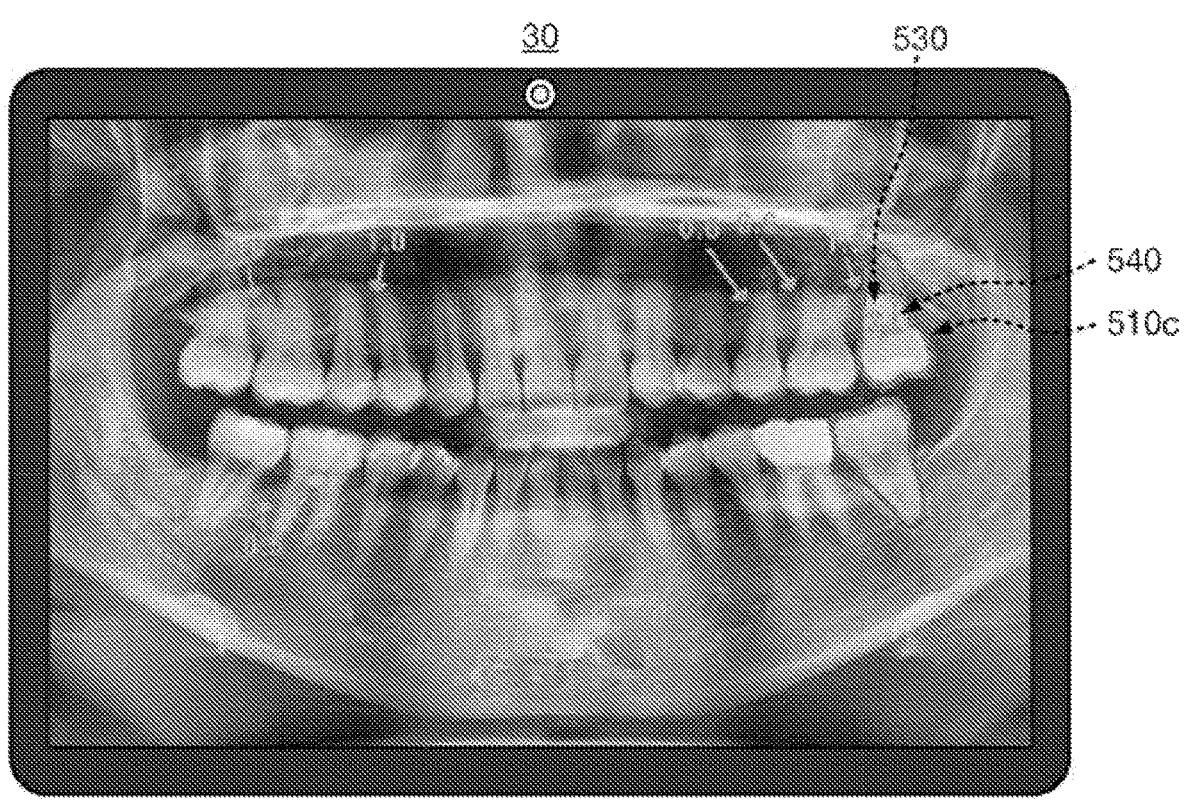

Referring to FIGS. 7A and 7B, when the selection signal 610 is input, the terminal device 30 may represent height information on a first gum bone in a second information representation region 530 and may represent height information on a second gum bone in a third information representation region 540. In this regard, the result oral x-ray image may be changed and the changed result oral x-ray image may be displayed.

Here, the height information on the first gum bone may be information relating to the height of the first gum bone which is the height of the gum bone in the third tooth in the previous period and the height information on the second gum bone may be information relating to the height of the second gum bone which is the height of the gum bone in the third tooth in the present period.

Figure 8:
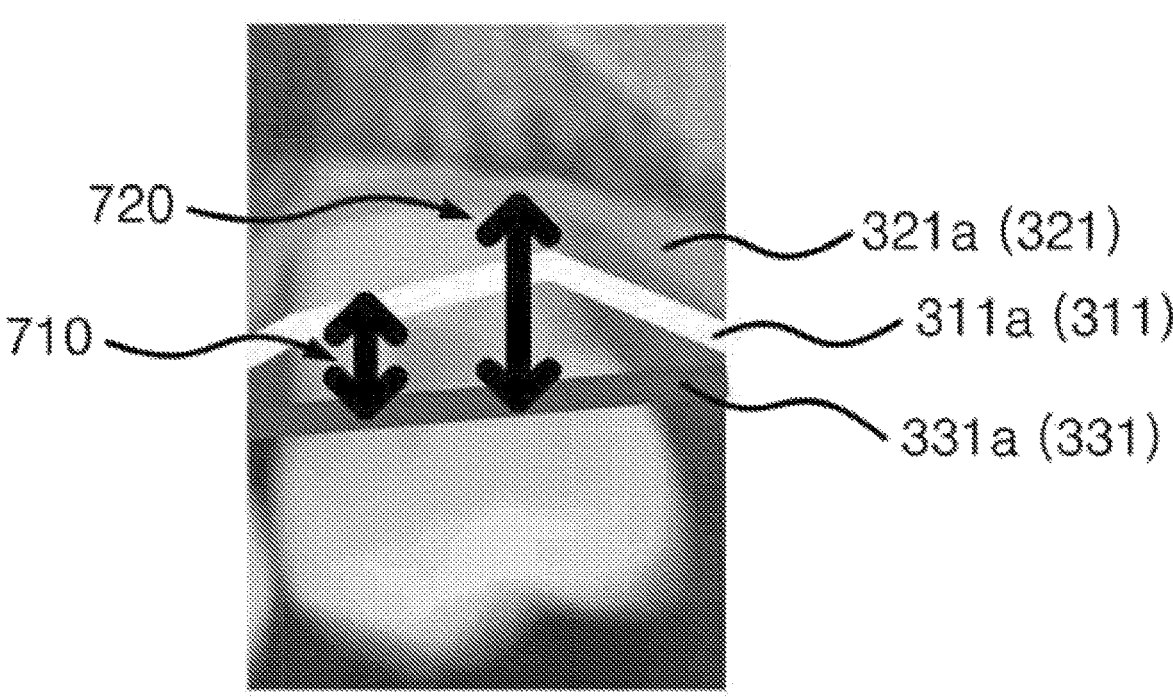

For example, referring to FIG. 8, a height 710 of the first gum bone may correspond to the length between a sub line 311a of the first gum bone that corresponds to the third tooth in the first gum bone line 311 and a sub line 331a of a normal gum bone that corresponds to the third tooth in a predetermined normal gum bone line 331. Also, a height 720 of the second gum bone may correspond to the length between a sub line 321a of the second gum bone that corresponds to the third tooth in the second gum bone line 321 and the sub line 331a of the normal gum bone. In this case, calculating average length according to a plurality of sample points described in FIG. 4 may be used to calculate the heights 710 and 720 of the first and second gum bones.

More specifically, referring to FIG. 7A, the height information on the first gum bone may correspond to a height value of the first gum bone of the third tooth, the height information on the second gum bone may correspond to a height value of the second gum bone of the third tooth, and the second and third information representation regions 530 and 540 may be adjacent to the third tooth region 510C at the outside of the third tooth region 510C.

Also, referring to FIG. 7B, the height information on the first gum bone may correspond to a first arrow line that represents the height of the first gum bone in the third tooth, the height information on the second gum bone may correspond to a second arrow line that represents the height of the second gum bone in the third tooth, and the second and third information representation regions 530 and 540 may be located at the inside of the third tooth region 510C.

According to an embodiment of the present invention, the terminal device 30 may determine whether the heights of the first and second gum bones are more than a predetermined critical height. Here, the critical height may correspond to initial height when periodontitis occurs (for example, 0.9 mm). When the height of the first or second gum bone is more than a critical height, the height information on the first or second gum bone may be represented with the first color (blue) which is the same as the periodontitis deterioration numeric values of the first information representation region 520 (refer to FIGS. 6A and 6B). On the other hand, when the height of the first or second gum bone is not more than a critical height, the height information on the first or second gum bone may be represented with a second color (for example, white) which is different from the first color. In case of FIGS. 7A and 7B, the third tooth that corresponds to the third tooth region 510C is a tooth corresponding to the gum where periodontitis is diagnosed and thereby, the heights of the first and second gum bones may be more than a critical height. Accordingly, the terminal device 30 may represent the height information of the first and second gum bones with the first color (blue).

Hereinafter, for convenience of description, it is assumed that the height information of the first and second gum bones is represented as in FIG. 7A.

Figure 9A:
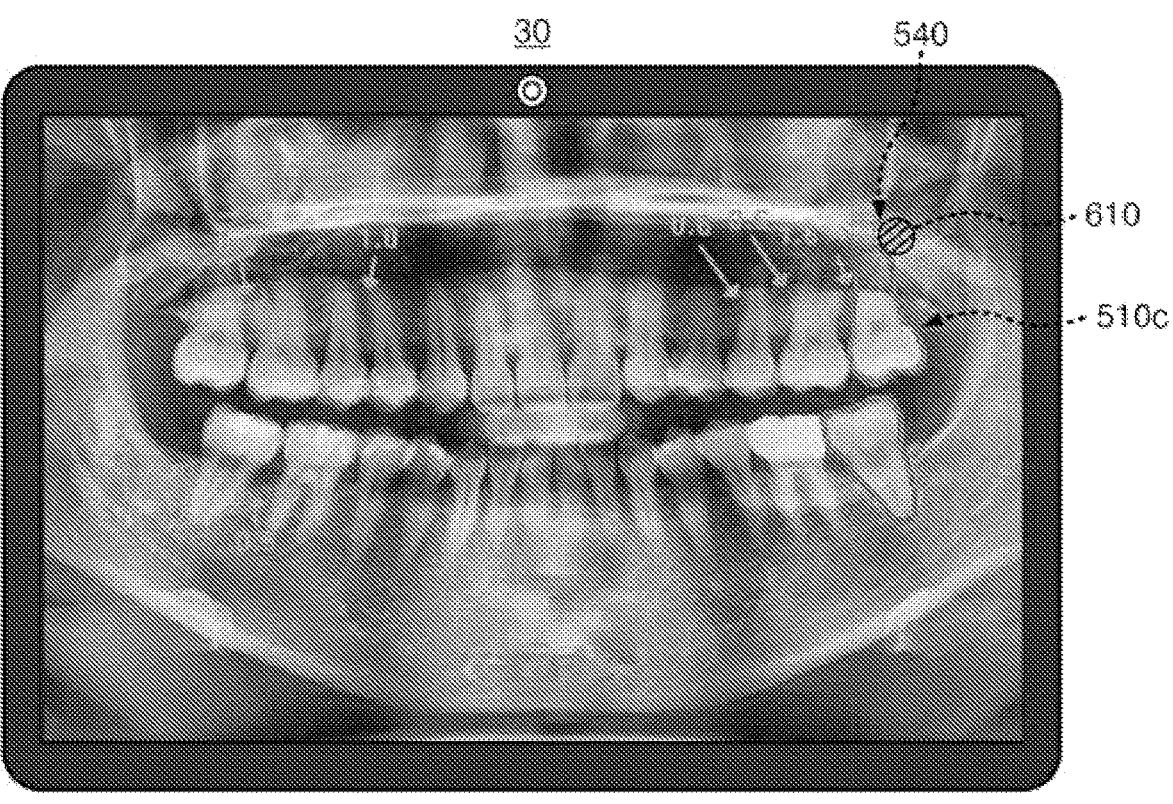

Then, referring to FIG. 9A, the selection signal 610 for the third information representation region 540 may be input by a medical staff. In this case, referring to FIG. 9B, the terminal device 30 may represent a real picture 910 of the gum of the third tooth in the second period to be adjacent to the third information representation region 540, may re-change the changed result oral x-ray image, and may display the re-changed result oral x-ray image. Here, the real picture 910 of the gum may be previously stored in the terminal device 30 or the management server 40.

Figure 9B:
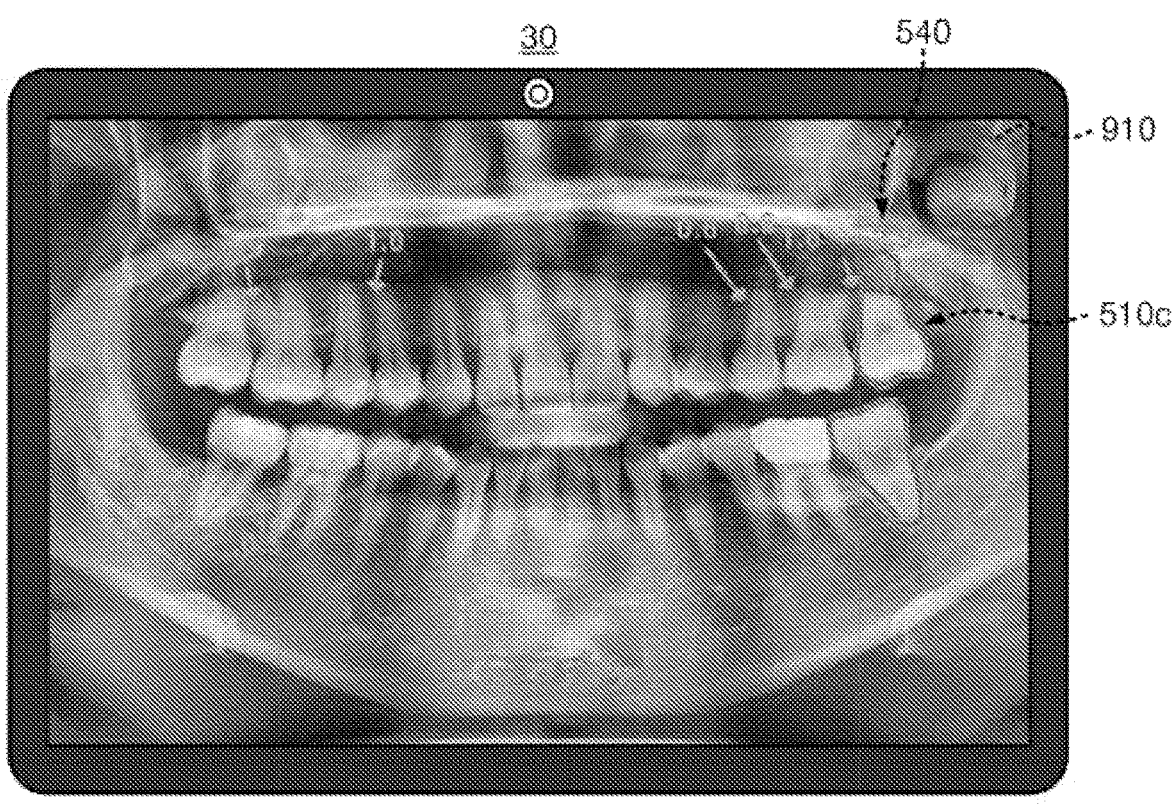

Although not illustrated in FIGS. 9A and 9B, the selection signal 610 for the second information representation region 530 may be input by a medical staff. In this case, the terminal device 30 may represent a real picture of the gum of the third tooth in the first period to be adjacent to the second information representation region 530, may re-change the changed result oral x-ray image, and may display the re-changed result oral x-ray image. Detailed description thereof is omitted due to similarity to the description of FIGS. 9A and 9B.

Figure 10A:
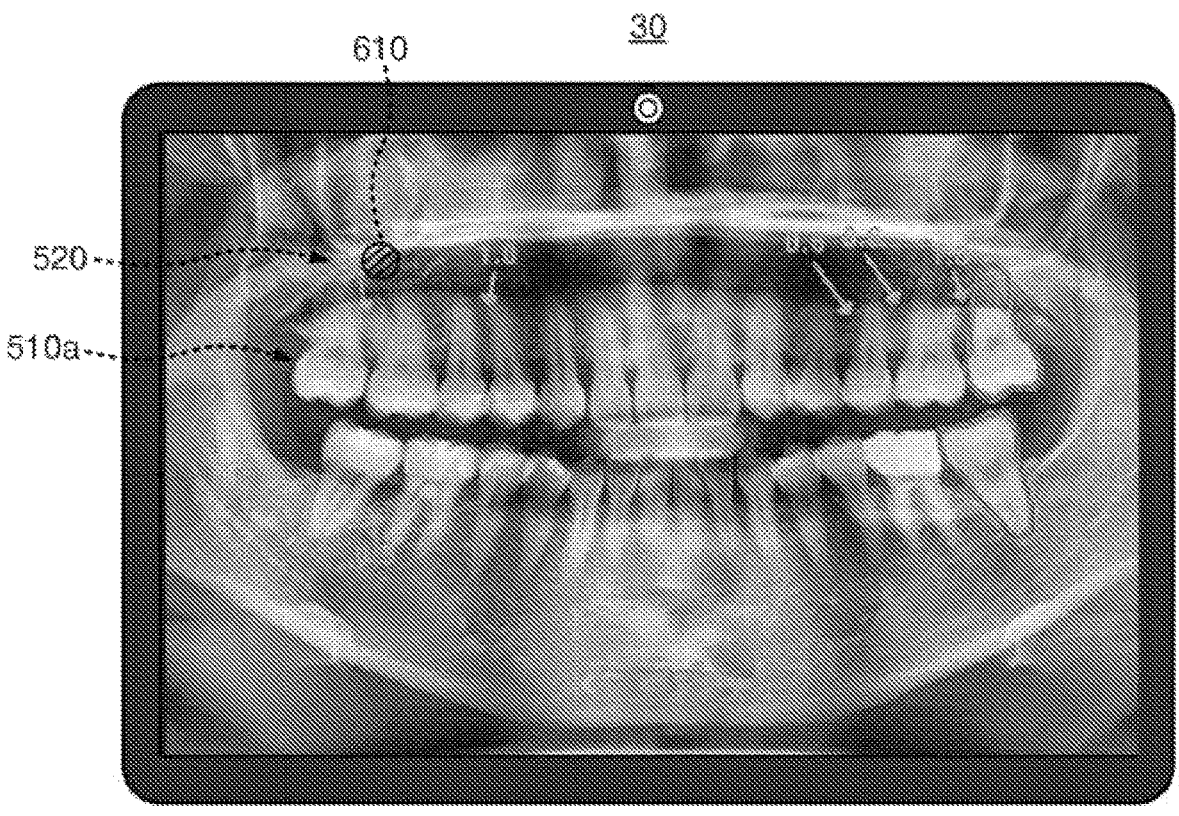
Figure 10B:
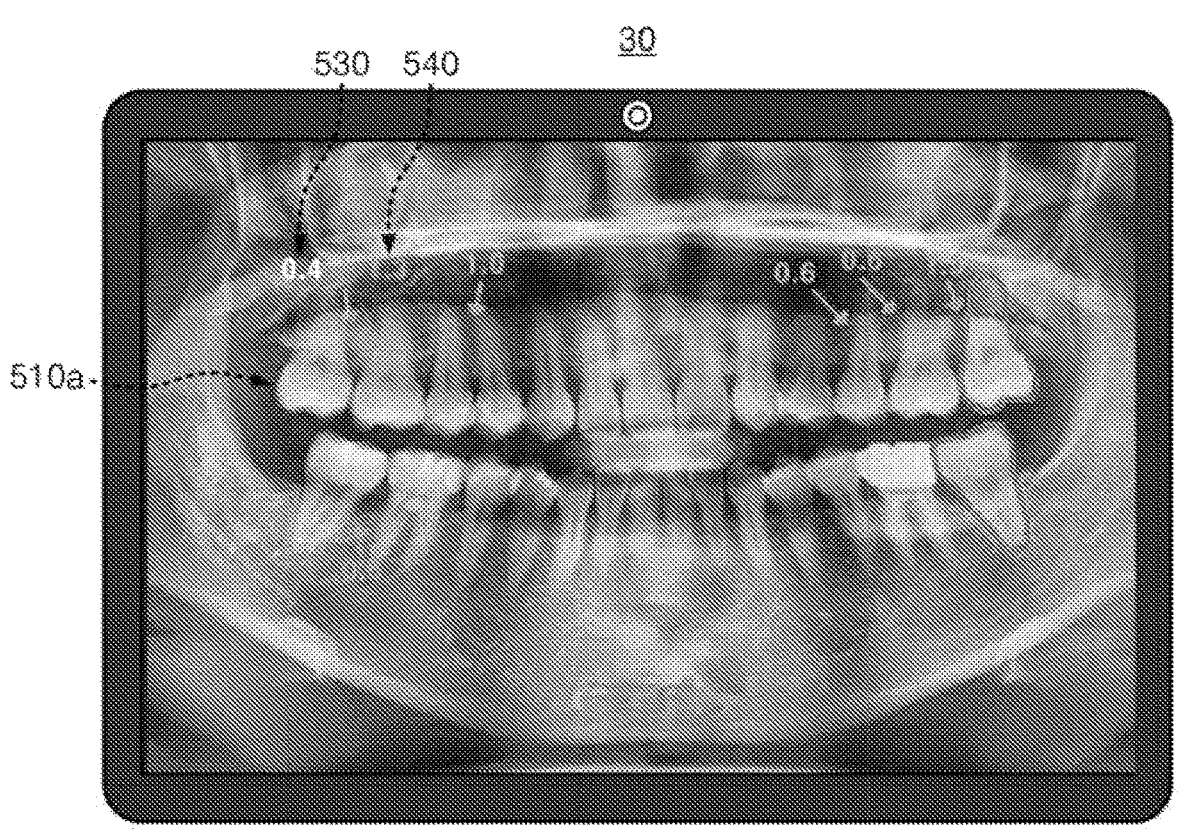

FIGS. 10A and 10B illustrate examples of displaying information relating to the first tooth region 510A according to an embodiment of the present invention.

Referring to FIG. 10A, the selection signal 610 from a medical staff may be input to the first information representation region 520 which is adjacent to the first tooth region 510A. In the first tooth region 510A, a unique selection region may not exist and the selection signal 610 may be input only to the first information representation region 520.

When the selection signal 610 is input, the terminal device 30 may represent the height information of the first gum bone in the second information representation region 530, may represent the height information of the second gum bone in the third information representation region 540, may change the result oral x-ray image, and may display the changed result oral x-ray image.

Here, the height of the first gum bone is not more than a critical height, the terminal device 30 may represent the height information of the first gum bone of the second information representation region 530 with the second color (white). Also, the height of the second gum bone is more than a critical height and thereby, the terminal device 30 may represent the height information of the second gum bone of the third information representation region 540 with the first color (blue).

Descriptions in FIGS. 6A through 9B may be applied to the embodiment of FIGS. 10A and 10B.

Figure 11A:
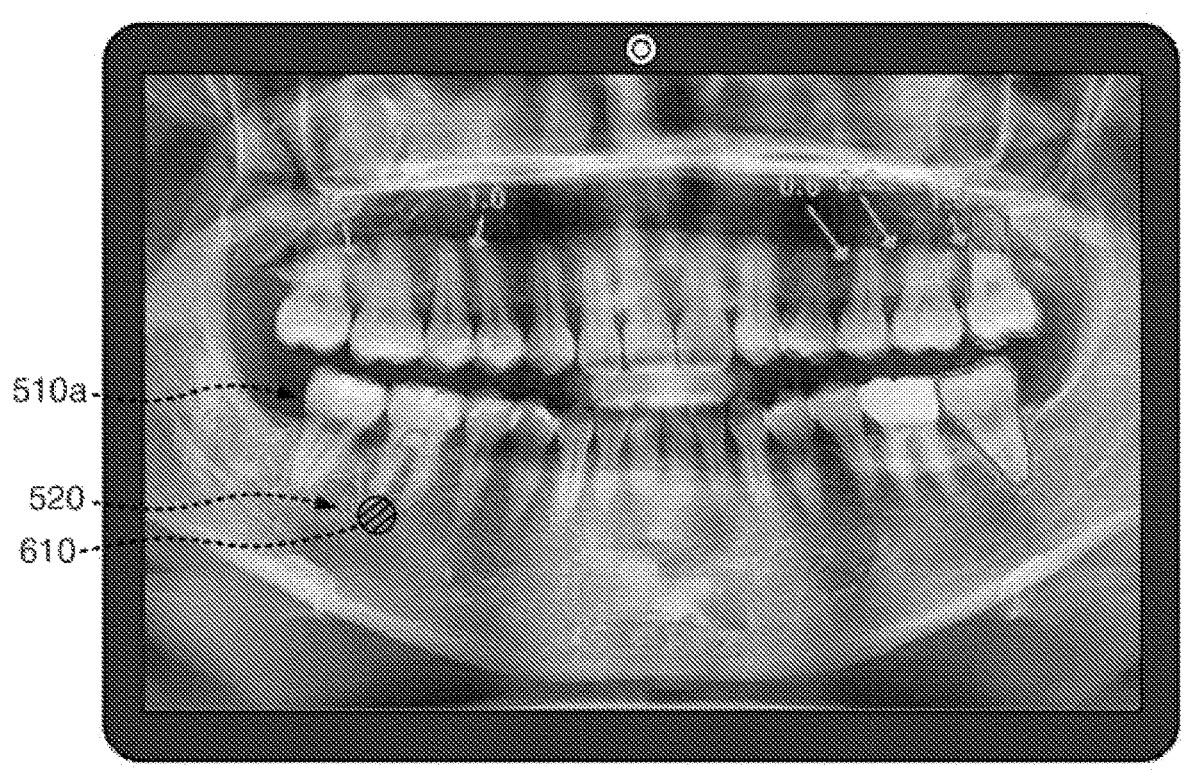
Figure 11B:
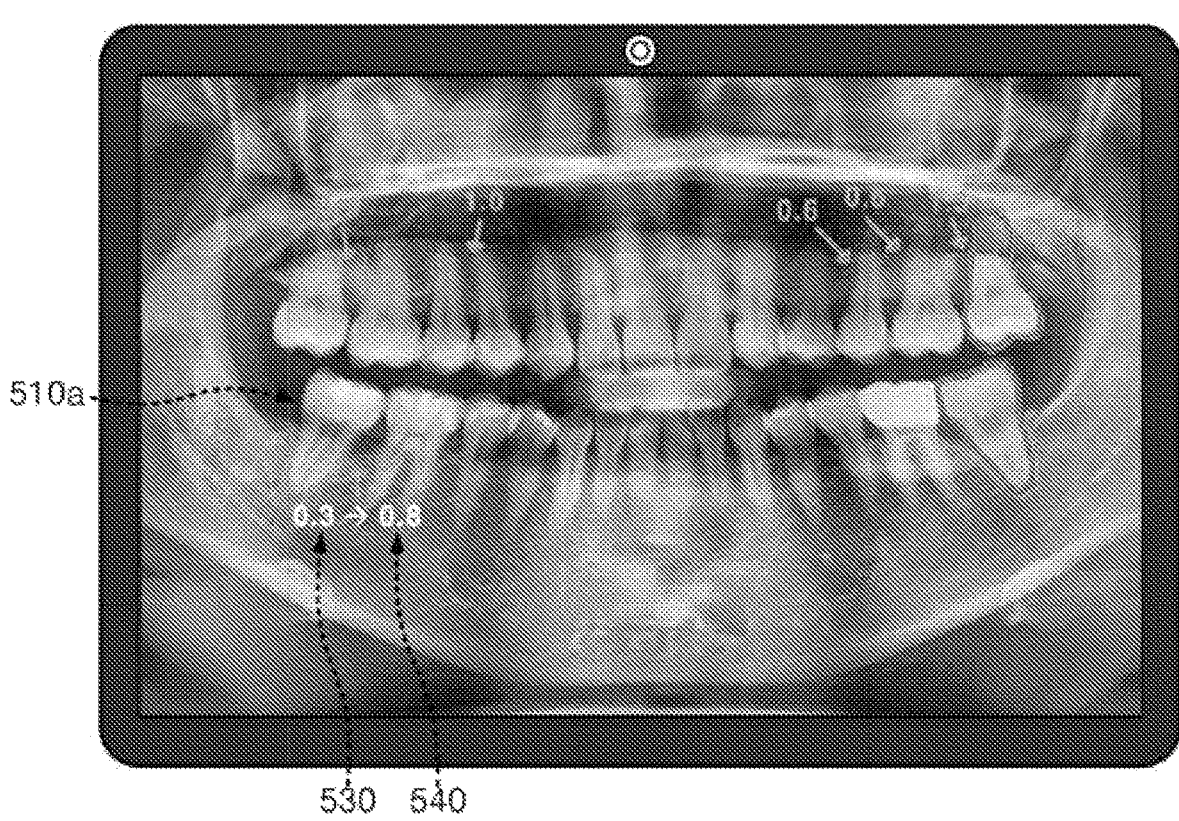

FIGS. 11A and 11B illustrate examples of displaying information relating to the first tooth region 510A according to another embodiment of the present invention.

Referring to FIG. 11A, the selection signal 610 from a medical staff may be input to the first information representation region 520 which is adjacent to the first tooth region 510A. In this case, the terminal device 30 may represent the height information of the first gum bone in the second information representation region 530, may represent the height information of the second gum bone in the third information representation region 540, may change the result oral x-ray image, and may display the changed result oral x-ray image.

Here, all of the heights of the first and second gum bones are not more than a critical height and thereby, the terminal device 30 may represent the height information of the first and second gum bones in the second and third information representation regions 530 and 540 with the second color (white).

Descriptions in FIGS. 6A through 9B may be applied to the embodiment of FIGS. 11A and 11B.

Figure 12A:
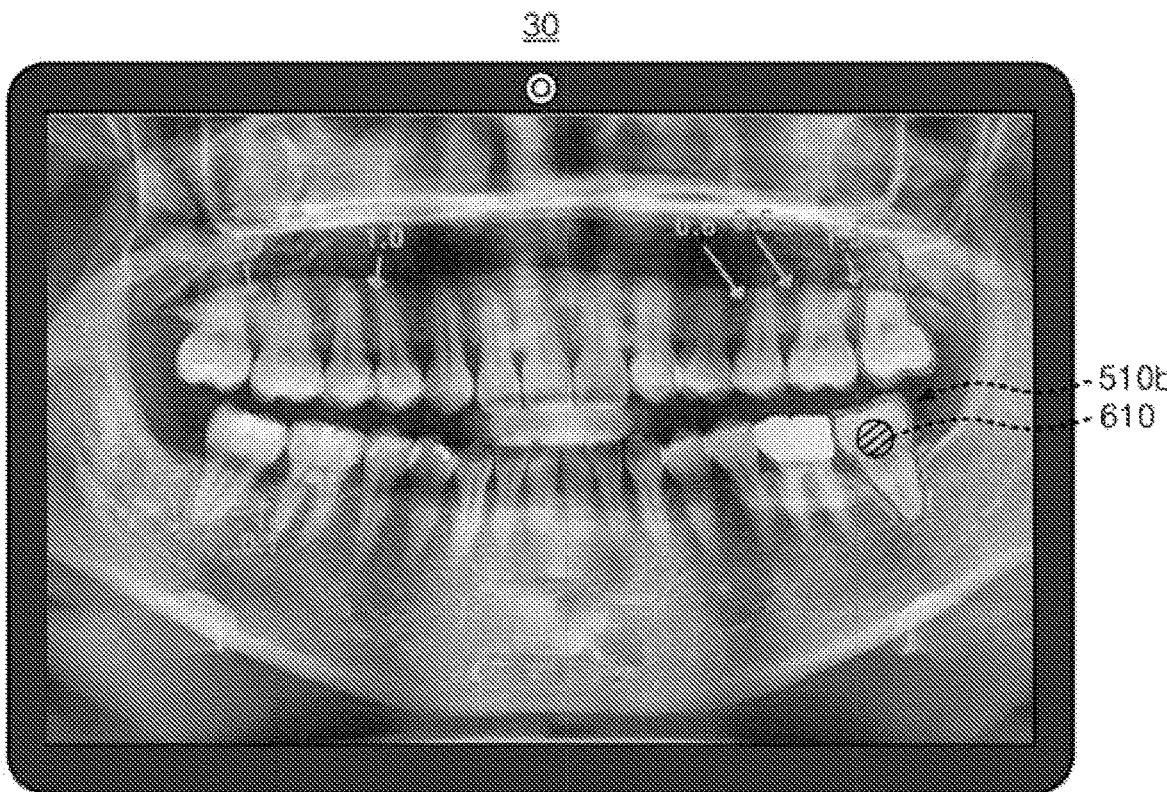
Figure 12B:
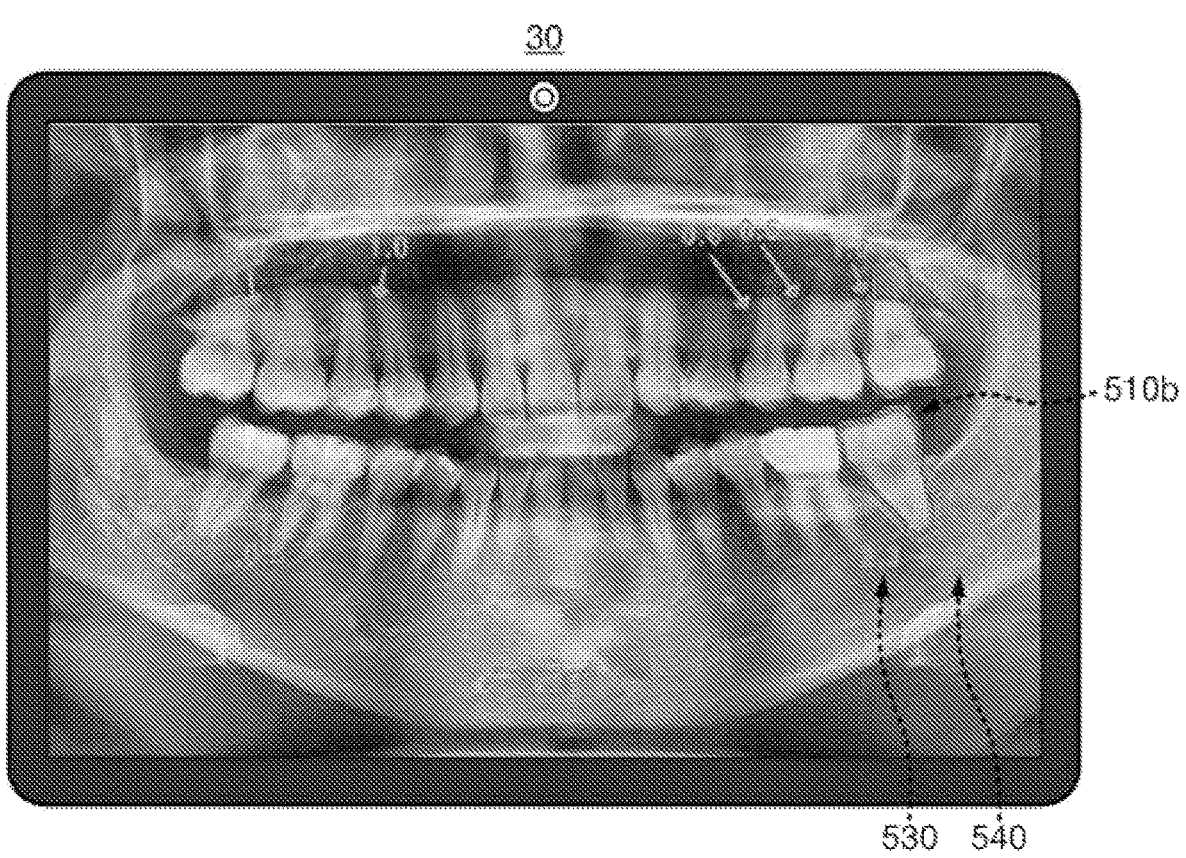

FIGS. 12A and 12B illustrate examples of displaying information relating to the second tooth region 510B according to an embodiment of the present invention.

Referring to FIG. 12A, the selection signal 610 from a medical staff may be input to the second tooth region 510B. The first information representation region 520 is not represented in the second tooth region 510B.

In this case, the terminal device 30 may represent the height information of the first gum bone in the second information representation region 530, may represent the height information of the second gum bone in the third information representation region 540, may change the result oral x-ray image, and may display the changed result oral x-ray image.

Here, the second tooth that corresponds to the second tooth region 510B is a tooth corresponding to the gum where periodontitis is diagnosed and thereby, the heights of the first and second gum bones may be more than a critical height. Accordingly, the terminal device 30 may represent the height information of the first and second burn bones with the first color (blue).

Descriptions in FIGS. 6A through 9B may be applied to the embodiment of FIGS. 12A and 12B.

To sum up, in the method of providing periodontitis information according to an embodiment of the present invention, the periodontitis deterioration numeric values for teeth that corresponds to the gums having a deteriorated periodontitis may be represented in the result oral x-ray image. Also, in the method of providing periodontitis information according to an embodiment of the present invention, when a degree of periodontitis is not deteriorated but periodontitis is diagnosed in the previous period, the periodontitis deterioration numeric values may be additionally represented in the result oral x-ray image in order to identify progress of oral state. Accordingly, medical staffs and users may easily identify the periodontitis deterioration numeric values of the first tooth and second tooth. In addition, the real pictures of the first tooth and second tooth are provided, medical staffs and users may accurately identify users' oral state.

FIG. 13 is a flowchart generally illustrating a method of operating a dental state mode, that is, a method of providing dental state information according to an embodiment of the present invention.

Here, all steps in the method of FIG. 13 may be executed in the terminal device 30. Also, a part of the steps in the method of FIG. 13 may be executed in the management server 40 or may be executed by being linked with the management server 40. Hereinafter, for convenience of description, it is assumed that steps in FIG. 13 are all executed in the terminal device 30.

Hereinafter, processes executed in each step will be described in more detail.

In step S202, the terminal device 30 may collect first dental state numeric values for users' teeth measured in the teeth diagnostic device 10 in the previous period (first period).

In step S204, the terminal device 30 may collect second dental state numeric values for users' teeth measured in the teeth diagnostic device 10 in the present period (second period).

In step S206, the terminal device 30 may select at least one fourth tooth from among users' teeth.

Here, the fourth tooth may be a tooth having a second dental state numeric value of not less than a predetermined dental state threshold numeric value from among users' teeth. Here, the dental state threshold numeric value may correspond to the lowest dental state numeric value which damages enamel of teeth.

In step S208, the terminal device 30 may calculate tooth deterioration numeric values for each of the at least one fourth tooth based on the first and second dental state numeric values for each of the at least one fourth tooth.

Here, the tooth deterioration numeric values are defined as information indicating how dental state of a user in the second period is deteriorated compared with dental state of a user in the first period. Generally, dental state may not get better naturally without treatment from a hospital. In this regard, the tooth deterioration numeric values may not have a negative value and may have a value above 0. In addition, as dental state is further deteriorated due to passage of time, the tooth deterioration numeric values may increase.

According to an embodiment of the present invention, the terminal device 30 subtracts the first dental state numeric values of the fourth tooth from the second dental state numeric values of the fourth tooth to calculate the tooth deterioration numeric values of the fourth tooth. According to another embodiment of the present invention, the terminal device 30 subtracts the first dental state numeric values of the fourth tooth from the second dental state numeric values of the fourth tooth by reflecting a weighted value to calculate the tooth deterioration numeric values of the fourth tooth.

Hereinafter, processes in step S206 and step S208 of FIG. 13 will be described in more detail with reference to FIG. 14.

Figures 14, 15:
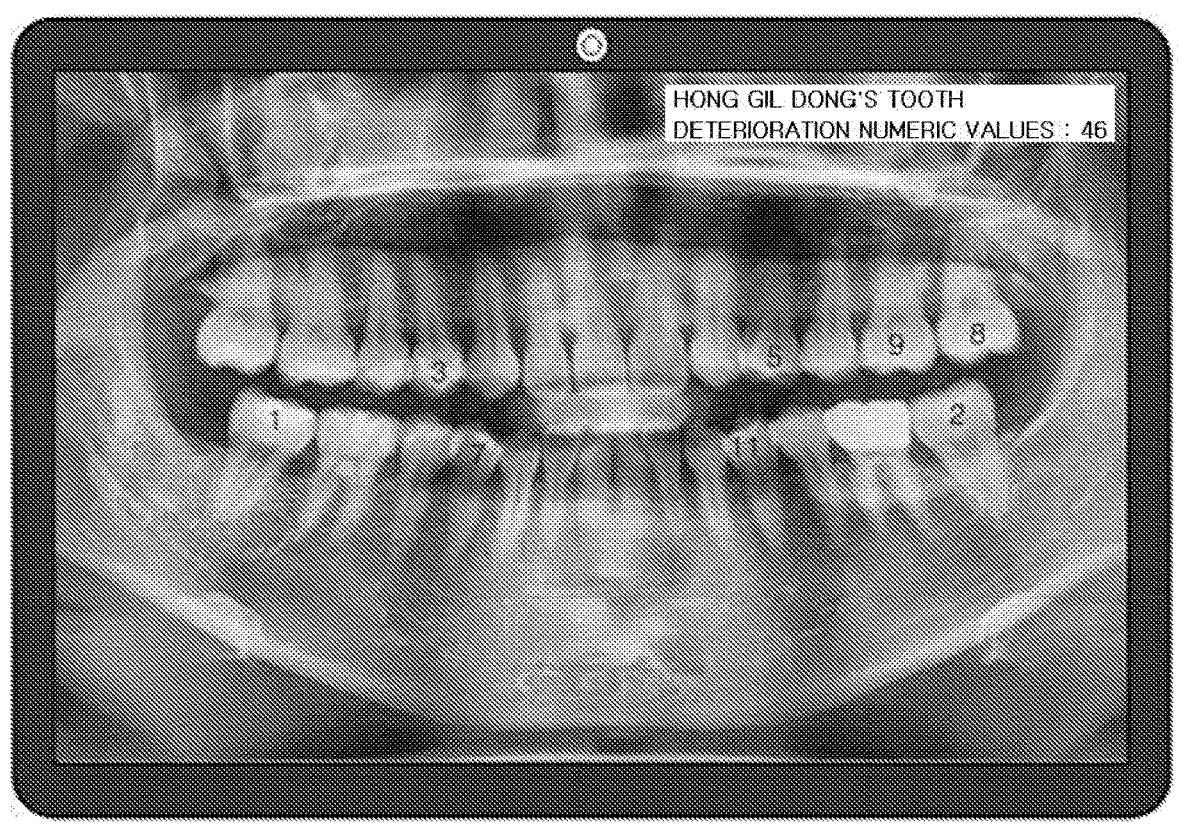
FIG. 14 is a table showing dental state measured numeric values in first and second periods for describing embodiments of the present invention.
FIG. 15 illustrates an example of a result oral x-ray image where tooth deterioration numeric values for each of at least one fourth teeth and users' tooth deterioration numeric values are represented according to an embodiment of the present invention.

Referring to FIG. 14, the first dental state numeric values for six teeth A, B, C, D, E, and G are measured in the first period. Dental state of a tooth F is not measured in the first period and thereby, the tooth F may have a first dental state numeric value which is a default value (=0). Then, the second dental state numeric values for seven teeth A, B, C, D, E, F, and G are measured in the second period. In case of the tooth G, the second dental state numeric value is lower than the first dental state numeric value. Accordingly, it may be inferred that the tooth G is treated from a hospital.

Here, if it is assumed that the dental state threshold numeric value is 25 points, the terminal device 30 may select four teeth (A, B, D, and E) as the fourth teeth where the second dental state numeric values thereof are not less than the dental state threshold numeric value (=25) from among seven teeth. Also, the terminal device 30 may calculate difference values between the second dental state numeric values and the first dental state numeric values for each of four fourth teeth (A, B, D, and E). In this regard, the tooth deterioration numeric values may be calculated for each of four fourth teeth (A, B, D, and E).

Referring back to FIG. 13, in step S210, the terminal device 30 may add the tooth deterioration numeric values for each of the at least one fourth tooth and may calculate the tooth deterioration numeric value of a user.

In the example of FIG. 13, the terminal device 30 may calculate a user's tooth deterioration numeric value as "27" which is obtained by adding the tooth deterioration numeric values for each of four fourth teeth (A, B, D, and E).

In step S212, the terminal device 30 may represent the tooth deterioration numeric values for each of the at least one fourth teeth in at least one corresponding tooth region from among the tooth regions of the second oral x-ray image, may represent the user's tooth deterioration numeric value in the second oral x-ray image, and thereby, may generate the result oral x-ray image (second result image). Also, in step S212, the terminal device 30 may display the result oral x-ray image. FIG. 15 illustrates an example of the result oral x-ray image where the tooth deterioration numeric values for each of the at least one fourth teeth and users' tooth deterioration numeric values are represented according to an embodiment of the present invention.

To sum up, in the method of providing dental state information according to an embodiment of the present invention, users' dental related state information measured in the teeth diagnostic device 10 is periodically collected and the dental state information, that is, the tooth deterioration numeric values for at least one fourth teeth and users' tooth deterioration numeric values may be simply and easily provided to medical staffs and users based on the periodically collected dental information.

In addition, when a tooth having the second dental state numeric value of not more than the dental state threshold numeric value (that is, tooth having a tooth decay) is used to calculate the user's tooth deterioration numeric value, a tooth deterioration degree of real users may not be accurately reflected. Accordingly, the terminal device 30 may only use at least one fourth tooth having the second dental state numeric value above the dental state threshold numeric value to calculate the user's tooth deterioration numeric value. The tooth having the second dental state numeric value of not more than the dental state threshold numeric value may not be used to calculate the user's tooth deterioration numeric value.

Also, as described above, the tooth deterioration numeric values are defined not to have a negative value. However, when teeth treated from a hospital is used to calculate users' tooth deterioration numeric values, the tooth deterioration numeric values may have a negative value. Accordingly, in order to prevent errors in calculation of the tooth deterioration numeric values and to accurately calculate users' tooth deterioration numeric values, teeth treated from a hospital may not be used to calculate users' tooth deterioration numeric values.

Figure 16:
FIG. 16 illustrates an example of an oral CT image of a user according to an embodiment of the present invention.

According to another embodiment of the present invention, in addition to the x-ray device 20 described above, various imaging devices for capturing user's oral image such as a CT device (refer to FIG. 16) for capturing user's oral CT image and a camera device for capturing a user's general oral image may be used. That is, the oral x-ray image described above may be included in oral images captured by various imaging devices. Also, above described method and the terminal device 30 which executes the method may provide the oral state information including periodontitis based on the oral images.

According to the present invention, information obtained by comparing the previous state of the gum and the present state of the gum may be simply and easily calculated based on periodically captured users' oral images and may be provided to users and medical staffs.

Also, according to the present invention, meaningful information relating to the gum, in particular, periodontitis deterioration numeric values, may be provided to users and medical staffs based on measured gum state.

In addition, effects of the present invention are not limited to above mentioned effects and it should be understood that all effects deducible from the detailed description of the invention and claims are included.

The embodiments of the present invention can also be embodied as program commands which may be executed through various computer means and can be recorded to a computer readable recording medium. The computer readable recording medium may include program commands, data file, or data structure, or a combination thereof. The program commands recorded to the medium may be specially designed and organized for the present invention or may be well-known to those skilled in a computer software field. Examples of the computer readable recording medium include magnetic media such as hard disks, floppy disks, and magnetic tapes, optical recording media such as CD-ROMs and DVDs, magneto-optical media such as floptical disks, and hardware devices specially designed for storing and executing program commands such as read-only memory (ROM), random-access memory (RAM), and flash memory. Examples of the program commands include not only machine language code made by a compiler but also high level language code executable by a computer using an interpreter. In order to perform operations in the embodiments of the present invention, the hardware devices may be formed to be operated as at least one software module or vice versa.

Hereinafter, although embodiments of the present invention have been described in detail, those of ordinary skill in the art to which the present invention pertains will understand that various modifications are capable of being made to the above-described embodiments without departing from the scope the present disclosure. Therefore, the scope of the present invention should not be limited to the described embodiments, but it should be defined by not only the claims described below, but also the claims and equivalents.

What is claimed is:

1. A method of providing periodontitis information executed in a processor based device comprising:

extracting a first gum bone line from user's first oral image captured in a first period;

extracting a second gum bone line from user's second oral image captured in a second period after the first period;

calculating a height difference in gum bones for each of the user's teeth based on the second gum bone line and the first gum bone line;

selecting a first tooth having a height difference in gum bones that is more than a predetermined threshold value from among user's teeth;

generating information on periodontitis deterioration numeric values of the first tooth based on the height difference of the gum bones in the first tooth;

generating a result oral image by representing information on periodontitis deterioration numeric values of the first tooth in a first information representation region which is adjacent to a first tooth region that corresponds to the first tooth in the second oral image;

displaying the result oral image;

representing height information on a first gum bone in a second information representation region, representing height information on a second gum bone in a third information representation region, and thereby changing the result oral image, when a selection signal for the first information representation region is input; and displaying the changed result oral image, wherein the height information on the first gum bone corresponds to a height of the gum bone in the first tooth in the first period and the height information on the second gum bone corresponds to a height of the gum bone in the first tooth in the second period.

2. The method of claim 1, wherein the information on periodontitis deterioration numeric values corresponds to the height difference in gum bones or a height difference level that corresponds to the height difference in gum bones.

3. The method of claim 1, wherein the second and third information representation regions are adjacent to the first tooth region at the outside of the first tooth region and the height information on the first and second gum bones corresponds to a height value of gum bones.

4. The method of claim 1, wherein the second and third information representation regions are located at the inside of the first tooth region and the height information on the first and second gum bones corresponds to arrow lines representing height of the gum bones.

5. The method of claim 1, wherein the height of the gum bone in the first tooth in the first period corresponds to the length between a sub line of a first gum bone that corresponds to the first tooth in the first gum bone line and a sub line of a normal gum bone that corresponds to the first tooth in a predetermined normal gum bone line and the height of the gum bone in the first tooth in the second period corresponds to the length between a sub line of a second gum bone that corresponds to the first tooth in the second gum bone line and a sub line of the normal gum bone.

6. The method of claim 1, wherein when the height of the gum bone in the first tooth that corresponds to the height information on the first or second gum bone is more than a predetermined threshold height that corresponds to initial height when periodontitis occurs, the height information on the first or second gum bone is represented with a predetermined first color and when the height of the gum bone in the first tooth that corresponds to the height information on the first or second gum bone is not more than the predetermined threshold height, the height information on the first or second gum bone is represented with a predetermined second color, wherein the first color and the second color are different from each other.

7. The method of claim 1, further comprising after displaying the changed result oral image:

representing a real picture of the gum in the first tooth in the first period to be adjacent to the second information representation region and re-changing the changed result oral image, when the selection signal for the second information representation region is input; and displaying the re-changed result oral image.

8. The method of claim 1, further comprising after displaying the changed result oral image:

representing a real picture of the gum in the first tooth in the second period to be adjacent to the third information representation region and re-changing the changed result oral image, when the selection signal for the third information representation region is input; and displaying the re-changed result oral image.

9. The method of claim 1, wherein in generating the result oral image, a second tooth region that corresponds to a second tooth from among user's teeth is represented to be distinguished from other tooth region and the second tooth is a tooth corresponding to the gum where periodontitis is diagnosed in the first period.

10. The method of claim 9, wherein in generating the result oral image, a boundary line of the second tooth region is represented with a predetermined third color.

11. The method of claim 9, further comprising after displaying the result oral image:

representing the height information on the first gum bone in the second information representation region, representing the height information on the second gum bone in the third information representation region, and changing the result oral image, when the selection signal for the second tooth region is input; and displaying the changed result oral image, wherein the height information on the first gum bone corresponds to a height of the gum bone in the first tooth in the first period and the height information on the second gum bone corresponds to a height of the gum bone in the first tooth in the second period.

12. A terminal device comprising:

a memory for storing computer readable commands;

a processor embodied to execute the commands; and a display unit for displaying execution results of the commands, wherein the processor, when the commands are executed, is configured to:

extract a first gum bone line from user's first oral image captured in a first period, extract a second gum bone line from user's second oral image captured in a second period after the first period, calculate a height difference in gum bones for each of the user's teeth based on the second gum bone line and the first gum bone line, select a first tooth having a height difference in gum bones that is more than a predetermined threshold value from among user's teeth, generate information on periodontitis deterioration numeric values of the first tooth based on the height difference of the gum bones in the first tooth, generate a result oral image by representing information on periodontitis deterioration numeric values of the first tooth in a first information representation region which is adjacent to a first tooth region that corresponds to the first tooth in the second oral image, display the result oral image, represent height information on a first gum bone in a second information representation region, represent height information on a second gum bone in a third information representation region, and thereby change the result oral image, when a selection signal for the first information representation region is input, and display the changed result oral image, wherein the height information on the first gum bone corresponds to a height of the gum bone in the first tooth in the first period and the height information on the second gum bone corresponds to a height of the gum bone in the first tooth in the second period.

13. A method of providing oral state information executed in a processor based device comprising:

generating a first result image that represents periodontitis deterioration numeric values of user's gums;

generating a second result image that represents tooth deterioration numeric values of user's teeth; and displaying at least one of the first result image and the second result image, wherein generating the first result image comprises: extracting a first gum bone line from user's first oral image captured in a first period; extracting a second gum bone line from user's second oral image captured in a second period after the first period; calculating a height difference in gum bones for each of the user's teeth based on the second gum bone line and the first gum bone line; selecting a first tooth having a height difference in gum bones that is more than a predetermined threshold value from among user's teeth; generating information on periodontitis deterioration numeric values of the first tooth based on the height difference of the gum bones in the first tooth; and generating the first result image by representing information on periodontitis deterioration numeric values of the first tooth in a first information representation region which is adjacent to a first tooth region that corresponds to the first tooth in the second oral image, and wherein generating the second result image comprises: calculating a tooth deterioration numeric value for each of the at least one tooth in the second period based on first dental state numeric values for each of the at least one user's tooth in the first period and second dental state numeric values for each of the at least one tooth in the second period, calculating user's tooth deterioration numeric value by adding the tooth deterioration numeric value for each of the at least one fourth tooth, representing the tooth deterioration numeric value for each of the at least one tooth in at least one corresponding tooth region from among tooth regions in the second oral image, representing user's tooth deterioration numeric values in the second oral image, and generating the second result image.

\* \* \* \* \*